(12) United States Patent
Margolin et al.

(10) Patent No.: US 6,359,118 B2
(45) Date of Patent: *Mar. 19, 2002

(54) CARBOHYDRATE CROSSLINKED GLYCOPROTEIN CRYSTALS

(75) Inventors: Alexey L. Margolin, Newton; Chandrika Poorna Govardhan, Lexington, both of MA (US); Kalevi Visuri, Kantvik; Sinikka Uotila, Espoo, both of (FI)

(73) Assignee: Altus Biologies, Inc., Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,717

(22) Filed: May 19, 1999

Related U.S. Application Data

(63) Continuation of application No. 08/926,279, filed on Sep. 5, 1997, now abandoned.

(51) Int. Cl.$^7$ ............ C07K 1/00; C12N 11/00; A61K 38/16

(52) U.S. Cl. ........ 530/395; 530/402; 530/408; 530/813; 530/815; 530/816; 435/39; 435/174; 435/178; 435/181; 424/193.1; 424/194.1; 514/8; 514/9

(58) Field of Search .................. 530/395, 402, 530/403, 813, 815, 816; 435/39, 174, 178, 181; 424/193.1, 194.1; 514/8, 9

(56) References Cited

U.S. PATENT DOCUMENTS

| | | | |
|---|---|---|---|
| 4,713,249 A | 12/1987 | Schröder | 424/488 |
| 4,849,109 A | 7/1989 | Sleytr et al. | 210/650 |
| 5,066,490 A | 11/1991 | Neville et al. | 424/85.91 |
| 5,120,650 A | 6/1992 | Visuri | 435/176 |
| 5,270,194 A | 12/1993 | D'Alterio et al. | 435/188 |
| 5,405,766 A * | 4/1995 | Kallury et al. | 435/174 |
| 5,437,993 A | 8/1995 | Visuri | 435/234 |
| 5,601,846 A | 2/1997 | Milstein et al. | 424/499 |
| 5,618,710 A * | 4/1997 | Navia et al. | 435/174 |
| 5,734,026 A | 3/1998 | Florin-Robertsson et al. | 530/424 |
| 5,801,022 A | 9/1998 | Navia et al. | 435/108 |
| 5,827,531 A | 10/1998 | Morrison et al. | 424/450 |
| 5,932,212 A | 8/1999 | Khalaf | 424/94.6 |
| 6,004,768 A | 12/1999 | Navia | 435/18 |
| 6,140,475 A | 10/2000 | Margolin et al. | 530/402 |

FOREIGN PATENT DOCUMENTS

| | | |
|---|---|---|
| CA | 1 196 864 | 11/1985 |
| EP | 0 341 503 | 11/1989 |
| GB | 2225324 | 5/1990 |
| WO | WO 92/02617 | 2/1992 |
| WO | WO 96/18417 | 6/1996 |
| WO | WO 96/41873 | 12/1996 |
| WO | WO 97/44445 | 11/1997 |
| WO | WO 98/13119 | 4/1998 |
| WO | WO 98/42749 | 10/1998 |
| WO | WO 98/46732 | 10/1998 |

OTHER PUBLICATIONS

K. Xu and A.M. Klibanov, "pH control of the catalytic activity of cross–linked enzyme crystals in organic solvents." *J. Am. Chem. Soc.*, 118, pp. 9815–9819 (1996).

H.J. Hecht et al., "Crystal structure of glucose oxidase from *Aspergillus niger* refined at 2.3 Å resolution." J. Mol. Biol. 229, pp. 153–172 (1993).

H.J. Hecht et al., "The 3D structure of glucose oxidase from *Aspergillus niger*. Implications for the use of GOD as a biosensor enzyme." Biosensors & Bioelectronics, 8, pp. 197–203 (1993).

B. Kozulic et al., "Study of the carbohydrate part of yeast acid phosphatase." Biochem. & Biophys. Res. Comm., 122, pp. 1083–1090 (1984).

R.D. Marshall, "Glycoproteins." Annual Reviews in Biochemistry, 41, pp. 673–702 (1972).

P.V. Wagh et al., "Sugar residues on proteins." Critical Reviews in Biochemistry, 10, pp.307–377 (1981).

D.C. Chan et al., "Core structure of gp41 from the HIV envelope glycoprotein." *Cell*, 89, 263–273 (1997).

A. Dyer et al., "A thermal investigation of the stability of crystalline cross–linked carboxypeptidase A." *Thermochimica Acta*, 8, 455–464 (1974).

(List continued on next page.)

*Primary Examiner*—Christopher S. F. Low
*Assistant Examiner*—Abdel A. Mohamed
(74) *Attorney, Agent, or Firm*—Fish & Neave; James F. Haley, Jr.; Margaret A. Pierri

(57) ABSTRACT

The present invention relates to the field of carbohydrate crosslinked glycoprotein crystals. Advantageously, such crosslinked glycoprotein crystals display stability to harsh environmental conditions, while maintaining the structural and functional integrity of the glycoprotein backbone. According to one embodiment, this invention relates to methods for concentrating proteins that have been modified by carbohydrates and for releasing their activity at controlled rates. This invention also provides methods for producing carbohydrate crosslinked glycoprotein crystals and methods for using them in pharmaceutical formulations, vaccines, immunotherapeutics, personal care compositions, including cosmetics, veterinary pharmaceutical compositions and vaccines, foods, feeds, diagnostics, cleaning agents, including detergents and decontamination formulations. The physical and chemical characteristics of carbohydrate crosslinked glycoprotein crystals render them particularly useful as sorbents for separations, such as chiral chromatography, or affinity chromatography—which are based on specific interactions between the active binding site of the glycoprotein component of the crystals and the substance or molecule of interest. Such characteristics also render carbohydrate crosslinked glycoprotein crystals useful as catalytic and binding components for the production of biosensing devices.

24 Claims, No Drawings

OTHER PUBLICATIONS

G.F. Gao et al., "Crystal structure of the complex between human CD8αα and HLA–A2." *Nature*, 387, pp. 630–634 (1997).

D.J. Haas, "Preliminary studies on the denaturation of cross–linked lysozyme crystals." *Biophysical Journal*, 8, 549–555 (1968).

U. Heimgartner et al., "Reversible and irreversible cross–linking of immunoglobulin heavy chains through their carbohydrate residues." *Biochem. J.*, 267, pp. 585–591 (1990).

H–Y. Hsiao and G.P. Royer, "Immobilization of glycoenzymes through carbohydrate side chains." *Archives of Biochemistry and Biophysics*, 198, 379–385 (1979).

P.J. Kasvinsky and N.B. Madsen, "Activity of glycogen phosphorylase in the crystalline state." *J. Biol. Chem.*, 251, pp. 6852–6859 (1976).

J.J. Lalonde et al., "Cross–linked Enzyme crystals of lipases as catalysts for kinetic resolution of acids and alcohols." *Methods in Enzymology*, 286, pp. 443–464 (1997).

K.M. Lee et al., "Crosslinked crystalline horse liver alcohol dehydrogenase as a redox catalyst: activity and stability toward organic solvent." *Bioorganic Chemistry*, 14, 202–210 (1986).

A.L. Margolin, "Novel crystalline catalysts." TIBTECH, 14, pp. 223–230 (1996).

P. Messner et al., "Artificial antigens. Synthetic carbohydrate haptens immobilized on crystalline bacterial surface layer glycoproteins." *Carbohydrate Research*, 233, pp. 175–184 (1992).

R.A. Persichetti et al., "*Candida Rugosa* lipase: enantioselectivity enhancements in organic solvents." *Tetrahedron Letters*, 37, pp 6507–6510 (1996).

B.H. Shilton et al., "Crystallization of a soluble form of the Kex1p serine carboxypeptidase from *Saccharomyces cerevisiae*." *Protein Science*, 5, 395–397 (1996).

N.L. St. Clair and M.A. Navia, "Cross–linked enzyme crystals as robust biocatalysts." *J. Am. Chem. Soc.*, 114, 7314–7316 (1992).

V.P. Torchilin et al., "Principles of enzyme stabilization. V. The possibility of enzyme selfstabilization under the action of potentially reversible intramolecular cross–linkages of different length." *Biochimica et Biophysica Acta*, 568, 1–10 (1979).

E. Tuchsen and M. Ottesen, "Kinetic properties of subtilisin type carlsberg in the crystalline state." *Carlsberg Res. Commun.*, 42, 407–420 (1977).

K. Xu and A.M. Klibanov, "pH control of the catalytic activity of cross–linked enzyme crystals in organic solvents." *J. Am. Chem. Soc.*, 118, pp. 9815–9819 (1996).

Vilenchi et al, *J. Am. Chem. Soc.*, vol. 120, pp. 4290–4294, 1998.*

McPherron, Jr. et al., *Methods of Biochemical Analyson*, vol. 23. pp. 249–345, 1976.*

Lalonde et al., *J. Am. Chem. Soc.*, vol. 117, pp. 6845–6852, 1995.*

Messner et al., *Appl. Microbiol. Biotechnicol*, vol. 40, pp. 7–11, 1993.*

Shib Pillai, *Biochem. J.*, vol. 193, pp. 825–828, 1981.*

* cited by examiner

CARBOHYDRATE CROSSLINKED GLYCOPROTEIN CRYSTALS

CROSS-REFERENCE TO RELATED APPLICATIONS

This is a continuation of U.S. application Ser. No. 08/926,279, filed Sep. 5, 1997, now abandoned.

TECHNICAL FIELD OF THE INVENTION

The present invention relates to the field of carbohydrate crosslinked glycoprotein crystals. Advantageously, such crosslinked glycoprotein crystals display stability to harsh environmental conditions, while maintaining the structural and functional integrity of the glycoprotein backbone. According to one embodiment, this invention relates to methods for concentrating proteins that have been modified by carbohydrates and for releasing their activity at controlled rates. This invention also provides methods for producing carbohydrate crosslinked glycoprotein crystals and methods for using them in pharmaceutical formulations, vaccines, immunotherapeutics, personal care compositions, including cosmetics, veterinary pharmaceutical compositions and vaccines, foods, feeds, diagnostics, cleaning agents, including detergents and decontamination formulations. The physical and chemical characteristics of carbohydrate crosslinked glycoprotein crystals render them particularly useful as sorbents for separations, such as chiral chromatography, or affinity chromatography—which are based on specific interactions between the active binding site of the glycoprotein component of the crystals and the substance or molecule of interest. Such characteristics also render carbohydrate crosslinked glycoprotein crystals useful as catalytic and binding components for the production of biosensing devices.

BACKGROUND OF THE INVENTION

Many proteins associated with the external surfaces of cell membranes or actively secreted from cells are commonly modified by the addition of one or more carbohydrate units to the side chains of particular amino acids [R. D. Marshall, *Ann. Rev. Biochem.*, 41, pp. 673–702 (1972)]. Such proteins, known as glycoproteins, display the properties of proteins in general, as well as properties typical of the attached carbohydrate. The carbohydrate monomers typically attached to glycoproteins include galactose, mannose, glucose, N-acetylglucosamine, N-acetylgalactosamine, fucose, xylose, sialic acid and others. The carbohydrate units are usually attached through the hydroxyl groups of serine and threonine side chains, or the amide nitrogen atom of asparagine side chains. The carbohydrate side chains are arranged in a variety of chain lengths and branching patterns [P. V. Wagh and O. P. Bahl, *Crit. Rev. Biochem.*, 10, pp. 307–77 (1981)].

Glycoproteins exhibit a range of protein functions, including catalysis of chemical transformations, proteolysis of proteins, binding of ligands and transport of ligands to and across membranes. Additionally, glycoproteins frequently perform functions associated with cellular communication, including protein-protein recognition, protein-carbohydrate recognition, protein-DNA recognition, pathogen recognition by antibodies, antigen presentation by CD4 and CD8 membrane glycoproteins, and targeting of proteins to specific locations.

Glucose oxidase exemplifies an enzyme glycoprotein that catalyzes the oxidation of β-D-glucose to D-glucono-1,5-lactone. The reaction consumes one mole of oxygen and produces one mole of hydrogen peroxide per mole of glucose. The active glycoprotein glucose oxidase, or β-D-glucose:oxygen 1-oxidoreductase [enzyme commission number 1.1.3.4] forms a dimer with a molecular weight of 150–180 kDa. Each monomer consists of 583 amino acids residues, one co-factor molecule of flavin adenine dinucleotide (FAD) and has a carbohydrate content of approximately 16% by weight. The three dimensional structure of the deglycosylated protein has been determined by X-ray crystallography [H. J. Hecht, H. M. Kalisz, J. Hendle, R. D. Schmid and D. Schomburg, *J. Mol. Biol.*, 229, pp.153–72 (1993)]. Due to the importance of the quantitative determination of glucose in medicine and industry, glucose oxidase is considered a prime candidate for the development of biosensors [H. J. Hecht, D. Schomburg, H. M. Kalisz and R. D. Schmid, *Biosensors and Bioelectronics*, 8, pp. 197–203 (1993)]. Glucose oxidase may be advantageously used in the food, drug and cosmetics industries, because of its ability to interconvert oxygen and hydrogen peroxide. Commercially available glucose oxidase is usually isolated from *Aspergillus niger*.

The stereoselectivity and specific activity of enzymatic glycoproteins may be exploited for use in industrial syntheses. For example, glutaraldehyde crosslinked crystals of Lipase from *Candida rugosa* may be used to synthesize optically pure compounds [J. J. Lalonde, C. Govardhan, N. Khalaf, A. G. Martinez, K. Visuri and A. L. Margolin, *J. Am. Chem. Soc.*, 117, (26) pp. 6845–52, (1995)].

In infectious diseases, glycoproteins are involved in the initiation and maintenance of infection, as well as host humoral and cellular immune responses against infection. The surface proteins of many viruses are glycoproteins. Examples of such glycoproteins include, for example, gp120 and gp41 of the Human Immunodeficiency Virus (HIV), which causes AIDS [H. Geyer, C. Holschbach, G. Hunsmann and J. Schneider, *J. Biol. Chem.*, 263 (24), pp. 11760–67, (1988)] and the hemagglutinin (HA) and neuraminidase (NA) of Influenza Virus, which causes Flu.

Viral receptors, the cellular proteins recognized by invading viruses, are found on the surface of cells and therefore are frequently either glycoproteins or carbohydrates. The CD4 molecule, which is recognized by HIV-1 gp120, is a glycoprotein. Similarly, Influenza virus hemagglutinin binds to terminal N-acetylneuraminic acid residues of sialoglycoproteins and enters the cell through receptor mediated endocytosis [J. White, M. Kielian and A. Helenius, *Ouart. Rev. of Biophys.*, 16, pp. 151–95, (1983)].

In spite of the tremendous medical, chemical, pharmaceutical and industrial potential of glycoproteins, their development has, in many instances, lagged far behind that of unglycosylated proteins.

As compared with unglycosylated proteins, the frequent association of glycoproteins with biological membranes and other membrane proteins, render glycoproteins significantly more difficult to purify and utilize for medical and industrial processes. The use of glycoproteins faces additional barriers because relatively little is known about their three-dimensional structure and the requirements for stabilization when faced with harsh environments. However, due to the specialized functions of glycoproteins, many benefits can be realized by overcoming the barriers to widespread large scale use of glycoproteins in industrial, chemical and medical applications.

One unique approach to overcoming barriers to the widespread use of proteins generally is crosslinked enzyme crystal ("CLEC™") technology [N. L. St. Clair and M. A. Navia, *J. Am. Chem. Soc.*, 114, pp. 4314–16 (1992)]. Crosslinked enzyme crystals retain their activity in environments that are normally incompatible with enzyme function. Such environments include prolonged exposure to proteases and other protein digestion agents, high temperature or extreme pH and organic solvents. In such environments, crosslinked enzyme crystals remain insoluble and stable.

One physical result of "CLEC™" technology is that the surface exposed amino acid side chains of the protein, in the crystal lattice, are covalently modified with the crosslinking agents. This modification stabilizes the crystal lattice, at the same time altering elements of the surface structure to gain the benefits of stabilization. For most applications involving protein crystals, any potential limitation resulting from minor surface modifications is overcome by the gains in stability achieved in the crystals. However, applications involving vaccines, and immunotherapeutics using glycoproteins, often require that the surface exposed protein structures, known as epitopes, precisely maintain the original structure. This may require stabilization without chemical modification of the amino acid side chains or perhaps with minor levels of chemical modification of the amino acid side chains.

DISCLOSURE OF THE INVENTION

The present invention specifically addresses the problems of stabilization of glycoproteins via crystallization and crosslinking for their use in industrial, chemical, and medical applications. Thus, the present invention relates to methods for crystallization of glycoproteins and for their subsequent stabilization through carbohydrate-to-carbohydrate crosslinking within the crystal lattice to produce carbohydrate crosslinked glycoprotein crystals.

Crosslinked glycoprotein crystals according to this invention may be produced by crosslinking glycoprotein crystals through one or more carbohydrate moieties on the glycoprotein or through both one or more carbohydrate moieties on the glycoprotein and one or more of the amino acid side chain functional groups in the glycoprotein.

The carbohydrate crosslinked glycoprotein crystals of this invention are useful in vaccines, pharmaceuticals and immunotherapeutic formulations for delivery of active, non-denatured, glycoproteins. They are also useful in biosensing devices and in methods, devices and systems for separating molecules of interest from mixtures or crude preparations thereof.

The present invention also includes methods for crystallizing glycoproteins in the absence of the potentially denaturing effects of chemical deglycosylation.

DETAILED DESCRIPTION OF THE INVENTION

In order that the invention herein described may be more fully understood, the following detailed description is set forth. In the description, the following terms or phrases are employed:

Aqueous-organic solvent mixture—a mixture comprising n % organic solvent, where n is between 1 and 99 and m% aqueous, where m is 100-n.

Catalytically effective amount—an amount of carbohydrate crosslinked glycoprotein crystals of this invention which is effective to treat, protect, repair or detoxify the area to which they are applied over some period of time.

Change in chemical composition—any change in the chemical components of the environment surrounding carbohydrate crosslinked glycoprotein crystals that affects the environment or the crosslinker, including addition of chemical reagents, solvent composition changes, chemical changes induced by application of energy in the form of light, microwave, or radiation to the environment, chemical events and parameters that affect the crosslinker and combinations thereof.

Change in shear force acting upon the crystals—any change in factors of the environment surrounding carbohydrate crosslinked glycoprotein crystals under conditions of use, such as, changes in mechanical pressure, both positive and negative, revolution stirring, centrifugation, tumbling, mechanical agitation and filtration pumping.

Controlled dissolution—dissolution of carbohydrate crosslinked glycoprotein crystals or release of the protein constituent of said crystals that is (1) triggered by a change in the environment surrounding said crystals, said change being selected from the group consisting of change in temperature, change in pH, change in chemical composition, change from concentrate to dilute form, change in shear force acting upon the crystals and combinations thereof and (2) controlled by a factor selected from the group consisting of the degree of crosslinking of said carbohydrate crosslinked glycoprotein crystals, the length of time of exposure of glycoprotein crystals to the crosslinking agent, the rate of addition of crosslinking agent to said glycoprotein crystals, the nature of the crosslinker, the chain length of the crosslinker, the surface area of said carbohydrate crosslinked glycoprotein crystals, the size of said carbohydrate crosslinked glycoprotein crystals, the shape of said carbohydrate crosslinked glycoprotein crystals and combinations thereof.

Formulations for decontamination—formulations selected from the group consisting of: formulations for decontamination of chemical wastes, herbicides, insecticides, pesticides, environmental hazards and chemical warfare agents.

Glycoprotein—a protein or peptide covalently linked to carbohydrate. The carbohydrate may be monomeric or composed of oligosaccharides.

Glycoprotein activity—an activity selected from the group consisting of binding, catalysis, signalling, transport, or other activities which induce a functional response within the environment in which the glycoprotein is used, such as induction of immune response and immunogenicity, or combinations thereof.

Glycoprotein activity release rate—the quantity of glycoprotein dissolved per unit time.

Insoluble and stable form of a alycoprotein—a form of a glycoprotein which is insoluble in aqueous solvents, organic solvents or aqueous-organic solvent mixtures and which displays greater stability than the soluble form of the glycoprotein. According to an alternate embodiment of this invention, the phrase "insoluble and stable form of a glycoprotein" may be a protein which is insoluble in dry formulations but soluble in wet formulations. In any embodiment, carbohydrate crosslinked glycoprotein crystals may be active in insoluble form. And in one embodiment, carbohydrate crosslinked glycoprotein crystals according to this invention may be active in insoluble form, then dissolve or are removed or digested once their function is complete.

Immunotherapeutic—a protein or glycoprotein derived from a tumor cell with a protein activity of inducing protective immunity to said tumor. A protein or glycoprotein cytokine which stimulates the immune system to reduce or eliminate said tumor.

Organic solvents—any solvent of non-aqueous origin.

Pharmaceutically effective amount—an amount of carbohydrate crosslinked glycoprotein crystals which is effective to treat a condition in an individual to whom they are administered over some period of time.

Prophylactically effective amount—an amount of carbohydrate crosslinked glycoprotein crystals which is effective to prevent a condition in an individual to whom they are administered over some period of time.

Protein—any peptide having a tertiary structure or any protein.

Separation—Separation of a substance from a mixture of two or more different substances or two or more forms of the same substance. According to another embodiment of this invention, "separation" is defined as purification of a substance from a crude form thereof. Separation may be carried out by any means including, for example, chromatography, membrane separation, filtration and electrophoresis.

Therapeutic alycoprotein—A glycoprotein which is administered to a patient in a conventional pharmaceutical formulation and manner. Therapeutic glycoproteins include, for example, hormones, enzymes, antibodies, viral receptors, T-cell receptors, chemokines, chemokine receptors, MHC molecules, tumor antigens, mucins, inhibitors, growth factors, trophic factors, cytokines, lymphokines, toxoids, nerve growth hormones, blood clotting factors, adhesion molecules, multidrug resistance proteins, adenylate cyclases and bone morphogenic proteins.

Vaccine antigen—a protein or glycoprotein derived from an infectious agent such as a virus, parasite, or tumor antigen. The protein activity of such vaccine antigens is to induce protective immunity against the infectious agent.

As a result of their crystalline nature, the carbohydrate crosslinked glycoprotein crystals of this invention achieve uniformity across the entire crosslinked crystal volume. This uniformity is maintained by the intermolecular contacts and chemical crosslinks between the carbohydrates attached to adjacent protein molecules constituting the crystal lattice, even when the crystals are exposed to buffers, organic or mixed aqueous-organic solvents and adjuvants. In such media, the glycoprotein molecules maintain a uniform distance from each other, forming well-defined stable pores within the carbohydrate crosslinked glycoprotein crystals that facilitate access of substrate or ligand to the glycoproteins, as well as removal of product.

The methods of this invention achieve stabilization of the crystal lattice by either exclusive crosslinking of attached carbohydrates of glycoproteins or a combination of carbohydrate and amino acid side chain crosslinking. In such carbohydrate crosslinked glycoprotein crystals, the lattice interactions, when fixed by chemical crosslinks, are particularly important in providing stability and preventing denaturation, especially in storage, under conditions including harsh environments created by components of compositions in which the crystals are used. The uniformity across crystal volume and enhanced stability of the constituent glycoproteins in carbohydrate crosslinked glycoprotein crystals creates novel opportunities for the use of glycoprotein vaccines, biosensors, and catalysis in harsh conditions, such as elevated temperature, and aqueous, organic or near-anhydrous solvents, as well as mixtures of these. Glycoprotein crystals may also be crosslinked in such a way that they dissolve or release their protein activity upon exposure to a trigger in their environment encountered under conditions of use. Thus, they may be substantially insoluble and stable in a composition under storage conditions and substantially soluble and active under conditions of use of said composition.

The methods of this invention advantageously accomplish the crystallization of glycoproteins, under large scale conditions, without the need for cumbersome and potentially denaturing effects of chemical deglycosylation. As a result, the carbohydrate moieties attached to amino acid side chains available for chemical crosslinking are maintained, while preserving those amino acid side chains not attached to carbohydrate in their unmodified form.

For those carbohydrate crosslinked glycoprotein crystals according to this invention which are enzymes, the entire crystal consists of active enzyme (and not inactive carrier). The specific activity per mg of immobilized protein product in carbohydrate crosslinked glycoprotein crystals is typically at least about 2 times higher than in conventionally immobilized proteins or catalysts, ranging from about 2 to 100 times higher. Such high glycoprotein densities are particularly useful in biosensor, analytical and other applications requiring large amounts of protein in small volumes.

Carbohydrate crosslinked glycoprotein crystals according to this invention offer several advantages over conventional protein/glycoprotein immobilization methods. For example, the crosslinked crystal matrix provides its own support. Expensive carrier beads, glasses, gels, or films are not required in order to tie down the enzyme catalyst, as they are in presently available immobilization methods. As a result, the concentration of glycoprotein is close to the theoretical packing limit that can be achieved for molecules of a given size, greatly exceeding densities achievable even in concentrated solutions.

In addition to their activity, carbohydrate crosslinked glycoprotein crystals according to this invention are particularly stable and insoluble under storage conditions, including the attendant storage temperature, storage pH, storage time, storage concentrate form, storage involving little or no shear force acting upon the crystals, or combinations thereof.

In addition to their stability under storage conditions, carbohydrate crosslinked glycoprotein crystals are particularly stable, at least about 2 times as stable, to thermal denaturation, digestion with proteases, for example pronase, and in mixed water:organic solvent mixtures. Specifically, the carbohydrate crosslinked glycoprotein crystals of this invention are between about 2 and 100 times as stable to thermal denaturation, between about 2 and 10,000 times more resistant to pronase digestion, and between about 2 and 1,000 times more stable to inactivation in 50% ethanol, than the soluble form of the enzyme.

The rate of dissolution of carbohydrate crosslinked glycoprotein crystals can be controlled by manipulating the conditions and extent of crosslinking. Controlled dissolution carbohydrate crosslinked glycoprotein crystals are slowly soluble and active under conditions of use, including conditions involving change in temperature, change in pH, change in chemical composition, change from concentrate to dilute form, change in shear force acting upon the crystals and combinations thereof. However such carbohydrate crosslinked glycoprotein crystals are insoluble and stable under storage conditions. Such properties make the carbohydrate crosslinked glycoprotein crystals of this invention particularly useful for delivery of pharmaceuticals, therapeutic glycoproteins, personal care agents or compositions, including cosmetics, vaccines, veterinary compositions, foods, feeds, diagnostics, cleaning agents, including detergents and formulations for decontamination.

According to one embodiment, the carbohydrate crosslinked glycoprotein crystals of this invention are characterized by a half-life of activity under storage conditions which is greater than at least about 2 times that of the soluble form of the glycoprotein that is crystallized to form the crystals that are crosslinked, as well as activity similar to that of the soluble form of the glycoprotein under conditions of use. Advantageously however, the carbohydrate crosslinked glycoprotein crystals of this invention display improved stability under storage conditions, as compared to their soluble or uncrosslinked crystallized counterpart glycoproteins.

Thus, carbohydrate crosslinked glycoprotein crystals according to this invention may be advantageously used instead of conventional soluble or immobilized proteins in pharmaceuticals, veterinary compounds, personal care compositions, including cosmetics, foods, feeds, vaccines, pulp, paper and textile processing, diagnostics, cleaning agents, including detergents and formulations for decontamination.

The carbohydrate crosslinked glycoprotein crystals of this invention are particularly advantageous because they are stable in harsh environments imposed by the formulations or compositions in which they are employed or conditions of their storage. At the same time, these carbohydrate crosslinked glycoprotein crystals are capable of (1) change to soluble and active form (an active form including, in one embodiment of this invention, a form which is active against macromolecular substrates) or (2) controlled dissolution or release of their activity when exposed to one or more triggers in their environment. Such triggers may be selected from the group consisting of change in temperature, change in pH, change in chemical composition, change from concentrate to dilute form, change in shear force acting upon the crystals and combinations thereof. Controlled dissolution or release of activity of carbohydrate crosslinked glycoprotein crystals according to this invention may also be triggered over a change in time.

Specific examples of such triggers include an increase or decrease in temperature, for example, an increase in temperature from a low temperature between about 0° C. and about 20° C. to a high temperature between about 25° C. and about 70° C. Other triggers include a change from acidic pH to basic pH and a change from basic pH to acidic pH. Examples of triggers of change from concentrate to dilute form include, for example, a change in solute concentration, a change in concentration of all solutes from about 2-fold to about 10,000-fold, a change in concentration of all solutes from about 2-fold to about 700-fold, an increase or decrease in salt concentration, an increase or decrease in water concentration, an increase or decrease in organic solvent concentration, a decrease in protein concentration and a decrease in detergent concentration.

Additional triggers involve changes in chemical composition of the environment surrounding the carbohydrate crosslinked glycoprotein crystals that affect the environment or the crosslinker itself. Such changes include, for example, addition of chemical reagents, increase or decrease in organic solvent concentration, chemical events that affect the crosslinker, chemical changes induced by application of energy, including light, microwave or radiation. As explained above, any of these triggers may act in combination or in sequence with one or more of the other triggers.

The glycoprotein constituent of the carbohydrate crosslinked glycoprotein crystals of this invention may be any glycoprotein, including for example, hormones, enzymes, antibodies, viral receptors, viral surface glycoproteins, parasite glycoproteins, parasite receptors, T-cell receptors, MHC molecules, immune modifiers, tumor antigens, mucins, inhibitors, growth factors, trophic factors, lymphokines, cytokines, toxoids, nerve growth hormones, blood clotting factors, adhesion molecules, multidrug resistance proteins, adenylate cyclases, bone morphogenic proteins and lectins.

Also included among the glycoproteins are the hormones and cytokines. Examples of hormones include follicle stimulating hormone, human chorionic gonadotropin, luteinizing hormone, thyrotrophin and ovine, bovine, porcine, murine and rat alleles of these hormones. Examples of cytokine glycoproteins include α-interferon, lymphotoxin, and interleukin-2. Also included are glycoprotein tumor-associated antigens, for example, carcinoembryonic antigen (CEA), human mucins, her-2/neu, and prostate-specific antigen (PSA) [R. A. Henderson and O. J. Finn, *Advances in Immunology*, 62, pp. 217–56 (1996)].

Alternatively, the glycoprotein constituent may be selected from personal care glycoproteins, including cosmetic glycoproteins, veterinary glycoproteins, food glycoproteins, feed glycoproteins, diagnostic glycoproteins, glycoproteins used in chemical reactions, glycoproteins used in industrial methods, cleaning agent glycoproteins, including detergent glycoproteins, and decontamination glycoproteins. Included among such glycoproteins are enzymes, such as, for example, hydrolases, transferases, isomerases, lyases, ligases, transferases and oxidoreductases. Examples of hydrolases include lipase, cholinesterase, alkaline phosphatase, β-amylase deoxyribonuclease, glucoamylase A and B, α-galactosidase I and II, β-fructofuranosidase, β-glucouronidase, N-acetyl-β-glucosaminidase, hyaluronidase, oxytocinase, kallikrein, bromelain, enterokinase, proteinase a, b, and c, pepsinogen and pepsin. Examples of oxidoreductases include glucose oxidase, peroxidase and chloroperoxidase. Examples of transferases include γ-glutamyltranspeptidase and ribonuclease.

In one embodiment of this invention, carbohydrate crosslinked glycoprotein crystals are produced by a method comprising at least one crosslinking reaction in which at least one carbohydrate moiety attached to the glycoprotein acts as or functions as the substrate for the crosslinking reaction. Multiple carbohydrate crosslinking reactions can be performed to modify further the characteristics of the carbohydrate crosslinked glycoprotein crystals.

The carbohydrate crosslinked glycoprotein crystals of this invention may be prepared using crosslinking reagents which are multifunctional or bifunctional agents. Such agents include the diamine group of compounds, such as, for example, hexamethylenediamine, diaminooctane, ethylenediamine, 4-(4-N-Maleimidophenyl)butyric acid hydrazide.HCl (MPBH), 4-(N-Maleimidomethyl) cyclohexane-1-carboxy-hydrazide.HCl ($M_2C_2H$),and 3-(2-Pyridyldithio)propionyl hydrazide (PDPH) and other amine alkenes.

In one embodiment of this invention, carbohydrate crosslinked glycoprotein crystals are produced by a method including at least one crosslinking reaction in which at least one carbohydrate moiety attached to the glycoprotein acts or functions as the substrate for the crosslinking reaction. One method of producing carbohydrate crosslinked glycoprotein crystals comprises an initial oxidation of the carbohydrate moieties, followed by crosslinking with at least a multifunctional reagent such as a diamine, followed by a reduction reaction using for example, $NaBH_4$. Alternatively, additional carbohydrate crosslinking reactions can be carried out as described but using different crosslinking reagents.

In another embodiment of this invention, carbohydrate crosslinked glycoprotein crystals are produced by a method including an initial crosslinking reaction in which one or more amino acid side chain functional groups serve as substrate for a multifunctional crosslinking reagent, such as glutaraldehyde. The first crosslinking reaction is followed by additional crosslinking reactions in which at least one involves crosslinking through one or more carbohydrate moieties and using, for example, a diamine crosslinking reagent.

In another embodiment of this invention, at least one crosslinking reaction is performed, in addition to the crosslinking reaction in which at least one oxidized carbohydrate moiety attached to the glycoprotein acts as or functions as the substrate for the crosslinking reaction, in which the amino acid side chain functional groups act as or function as a substrate for the crosslinking reaction. This additional linking can be achieved using one or a combination of a wide variety of multifunctional crosslinking reagents, at the same time (in parallel) or in sequence. Such multifunctional reagents include bifunctional reagents. Examples of such crosslinking agents are glutaraldehyde, succinaldehyde, octanedialdehyde and glyoxal. Additional multifunctional crosslinking agents include halo-triazines, e.g., cyanuric chloride; halo-pyrimidines, e.g., 2,4,6-trichloro/bromo-pyrimidine; anhydrides or halides of aliphatic or aromatic mono- or di-carboxylic acids, e.g., maleic anhydride, (meth)acryloyl chloride, chloroacetyl chloride; N-methylol compounds, e.g., N-methylol-chloro acetamide; di-isocyanates or di-isothiocyanates, e.g., phenylene-1,4-di-isocyanate and aziridines. Other crosslinking agents include epoxides, such as, for example, di-epoxides, tri-epoxides and tetra-epoxides. For a representative listing of other available crosslinking reagents see, for example, the *Pierce Cataloa and Handbook*, Pierce Chemical Company, Rockford, Ill. (1997) and also S. S. Wong, *Chemistry of Protein Conjugation and Cross-Linking*, CRC Press, Boca Raton, Florida (1991).

According to one embodiment of this invention, carbohydrate crosslinked glycoprotein crystals are produced by a method comprising at least one crosslinking reaction through one or more carbohydrate moieties in said glycoprotein, alone or in sequence with crosslinking via a multifuntional reagent such as glutaraldehyde or other crosslinkers that function by crosslinking one or more amino acid side chain functional groups in said glycoprotein.

According to an alternate embodiment of this invention, at least one non-carbohydrate crosslinking reaction may be carried out using reversible crosslinkers, in parallel or in sequence with the carbohydrate crosslinking reaction. The resulting carbohydrate crosslinked glycoprotein crystals are characterized by containing a reactive multifunctional linker, into which a trigger has been incorporated as a separate group. The reactive functionality is involved in linking together reactive amino acid side chains in a glycoprotein and the trigger consists of a bond that can be broken by altering one or more conditions in the surrounding environment (e.g., pH, temperature, or thermodynamic water activity).

Examples of reversible crosslinkers are described in T. W. Green, *Protective Groups in Organic Synthesis*, John Wiley & Sons (Eds.) (1981). Any variety of strategies used for reversible protecting groups can be incorporated into a crosslinker suitable for at least one crosslinking in producing carbohydrate crosslinked glycoprotein crystals capable of reversible, controlled solubilization. Various approaches are listed, in Waldmann's review of this subject, in *Angewante Chemie Inl. Ed. Engl.*, 35, p. 2056 (1996).

Other types of reversible crosslinkers are disulfide bond-containing crosslinkers. The trigger breaking crosslinks formed by such crosslinkers is the addition of reducing agent, such as cysteine, to the environment of the crosslinked protein crystals.

Disulfide crosslinkers are described in the *Pierce Catalog and Handbook* (1997). Examples of such crosslinkers include the symmetric homo-bifunctional, as for example DSS -dithiobis (succinimidyl-propionate), also know as Lomant's Reagent and DTSSP-3-3'-dithiobis (sulfo-succinimidylpropionate), a water soluble version of DSP and many more. Other examples include the heterobifunctional or asymmetric crosslinkers such as SPDP-N-succinimidyl-3-(2-pyridyldithio)propionate and LC-SPDP-succinimidyl-6-(3-[2-pyridyldithio] propionate)hexanoate and others.

In another embodiment of this invention, the dissolution, catalytic, antigenic and pharmaceutical properties of carbohydrate crosslinked glycoprotein crystals are modified by the specific combinations of crosslinking reactions performed.

Controlled dissolution of carbohydrate crosslinked glycoprotein crystals according to the present invention may also be effected by a change in time sufficient to permit a protein activity release rate between about 0.1% per day and about 100% per day, a change in time sufficient to permit a protein activity release rate between about 0.01% per hour and about 100% per hour or a change in time sufficient to permit a protein activity release rate between about 1% per minute and about 50% per minute.

Carbohydrate crosslinked glycoprotein crystals according to this invention, therefore, include those capable of releasing their protein activity at a controlled rate upon exposure to a change in their environment, said change being selected from the group consisting of change in pH, change in solute concentration, change in temperature, change in chemical composition, change in shear force acting upon the crystals and combinations thereof.

Factors contributing to the release rate of protein activity of carbohydrate crosslinked glycoprotein crystals according to this invention include the degree of crosslinking of the carbohydrate crosslinked glycoprotein crystals, whether the reduction step was performed after the crosslinking reaction, the pH used for the oxidation reaction, the pH used for the crosslinking reaction, the pH used for the reduction reaction, whether the multifunctional crosslinking agent was pretreated, the polymerization state of the crosslinking agent, the number of crosslinking reactions performed, the length of time of exposure of protein crystals to the crosslinking agent, the rate of addition of crosslinking agent or agents to the glycoprotein crystals, the length of time of exposure of glycoprotein crystals to the crosslinking agent, the nature of the crosslinker either carbohydrate specific or amino acid side-chain specific, the chain length of the crosslinker, the surface area of the carbohydrate crosslinked glycoprotein crystals, the size of the carbohydrate crosslinked glycoprotein crystals, the shape of the carbohydrate crosslinked glycoprotein crystals and combinations thereof.

According to this invention, any individual, including humans and other mammals, as well as birds and fish, for example, may be treated in a pharmaceutically acceptable manner with a pharmaceutically effective or a catalytically effective amount of carbohydrate crosslinked glycoprotein crystals for a period of time sufficient to treat a condition in the individual to whom they are administered over some period of time. Alternatively, individuals may receive a prophylactically effective or a catalytically effective amount of carbohydrate crosslinked glycoprotein crystals which is effective to prevent a condition in the individual to whom they are administered over some period of time.

Carbohydrate crosslinked glycoprotein crystals may be administered alone, as part of a pharmaceutical, personal care or veterinary preparation or as part of a prophylactic preparation, such as a vaccine, with or without adjuvant. They may be administered by parenteral or non-parenteral route. For example, they may be administered by oral, pulmonary, nasal, aural, anal, dermal, ocular, intravenous, intramuscular, intraarterial, intraperitoneal, mucosal, sublingual, subcutaneous, or intracranial route. In either pharmaceutical, personal care or veterinary applications, carbohydrate crosslinked glycoprotein crystals may be topically administered to any epithelial surface. Such epithelial surfaces include oral, ocular, aural, anal and nasal surfaces, to treat, protect, repair or detoxify the area to which they are applied.

Pharmaceutical combinations of the present invention may be formulated in a variety of conventional forms employed for parenteral administration. These include, for example, semi-solid and liquid dosage forms, such as liquid solutions or suspensions, suppositories, douches, enemas, gels, creams, emulsions, lotions, slurries, powders, and pastes. Standard formulation strategies for vaccines, immunotherapeutics and pharmaceuticals may be applied to carbohydrate crosslinked glycoprotein crystals in order to enhance the persistence and residence time of the active agent, and to improve the prophylactic efficacy achieved.

The present invention also includes controlled release formulations comprising carbohydrate crosslinked glycoprotein crystals. In such formulations, the carbohydrate crosslinked glycoprotein crystals are substantially insoluble under storage conditions and capable of releasing their protein activity in vivo at a controlled rate. For example, a pharmaceutical controlled release formulation according to this invention, administered by oral route, is characterized in that the component carbohydrate crosslinked glycoprotein crystals are substantially insoluble under gastric pH conditions and substantially soluble under small intestine pH conditions. Alternatively, for these and other uses according to this invention, the carbohydrate crosslinked glycoprotein crystals are biodegradable and may be active in the insoluble form and then dissolve and are removed or digested once their function is complete.

Pharmaceutical, personal care, veterinary or prophylactic compositions comprising carbohydrate crosslinked glycoprotein crystals according to this invention may also be selected from the group consisting of tablets, liposomes, granules, spheres, microparticles, microspheres and capsules.

For such uses, as well as other uses according to this invention, carbohydrate crosslinked glycoprotein crystals may be formulated into tablets. Such tablets constitute a liquid-free, dust-free form of carbohydrate crosslinked glycoprotein crystal storage, which are easily handled and retain acceptable levels of activity.

Alternatively, the carbohydrate crosslinked glycoprotein crystals may be in a variety of conventional depot forms employed for administration to provide reactive compositions. These include, for example, solid, semi-solid and liquid dosage forms, such as liquid solutions or suspensions, gels, creams, balms, emulsions, lotions, slurries, powders, sprays, foams, pastes, ointments, salves, balms and drops.

According to one embodiment of this invention, carbohydrate crosslinked glycoprotein crystals may be combined with any conventional materials used for controlled release administration of pharmaceutical glycoproteins. Such materials include, for example, coatings, shells and films, such as enteric coatings and polymer coatings and films.

The most effective mode of administration and dosage regimen of formulations or compositions comprising carbohydrate crosslinked glycoprotein crystals of this invention will depend on the effect desired, previous therapy, if any, the individual's health status or status of the condition itself and response to the carbohydrate crosslinked glycoprotein crystals and the judgment of the treating physician or clinician. The carbohydrate crosslinked glycoprotein crystals may be administered in any dosage form acceptable for pharmaceuticals, personal care compositions or veterinary formulations, at one time or over a series of treatments.

The amount of the carbohydrate crosslinked glycoprotein crystals that may be combined with carrier materials to produce a single dosage form will vary depending upon the particular mode of administration, formulation, dose level or dose frequency. A typical preparation will contain between about 0.01% and about 99%, preferably between about 1% and about 50%, carbohydrate crosslinked glycoprotein crystals (w/w).

Upon improvement of the individual's condition, a maintenance dose of carbohydrate crosslinked glycoprotein crystals may be administered, if necessary. Subsequently, the dosage or frequency of administration, or both, may be reduced as a function of the symptoms, to a level at which the improved condition is retained. When the condition has been alleviated, treatment should cease. Individuals may, however, require intermittent treatment on a long-term basis upon any recurrence of the condition or symptoms thereof.

The properties of the carbohydrate crosslinked glycoprotein crystals of this invention are especially suited for applications involving vaccines, to protect humans and animals from infectious diseases.

The methods of this invention may be used to produce carbohydrate crosslinked glycoprotein crystals from virus, or parasite glycoproteins for use as antigens in a vaccine. Appropriately spaced and repeated parenteral inoculations of carbohydrate crosslinked glycoprotein crystals in combination with immune system modifiers such as adjuvants and/or cytokines are useful to induce patient antibody and T-cell immune responses to viral, or parasite glycoproteins. The patient immune responses can prevent or mitigate transmission or disease from of an enveloped virus infection, or parasite infections.

Such enveloped viruses include, for example, virus from the genera Retroviridae, Herpesviridae, Orthomyxoviridae, Paramyxoviridae, Hepadnaviridae, Flaviviridae, Togaviridae, Rhabdoviridae, Poxviridae, Arenaviridae, Coronoviridae, Bunyaviridae and Filoviridae.

Retroviridae infections that may be prevented or treated using the methods of this invention include, for example, those caused by human immunodeficiency virus type 1 and the human immunodeficiency virus type 2 lentiviruses, foamy viruses and human T-cell leukemia viruses.

Herpesviridae infections that may be prevented or treated using the methods of this invention include, for example, those caused by herpes simplex type 1 and herpes simplex type 2 viruses, human herpes virus-6, Human herpes virus-8, varicella-zoster viruses, cytomegaloviruses, lymphoproliferative herpesviruses, Epstein-Barr virus and other herpes viruses.

Orthomyxoviridae infections that may be prevented or treated using the methods of this invention include, for example, those caused by influenza A, influenza B and influenza C viruses.

Paramyxoviridae infections that may be prevented or treated using the methods of this invention include, for example, those caused by respiratory syncytial virus, mumps virus, parainfluenza viruses and measles-like viruses.

Hepadnaviridae infections that may be prevented or treated using the methods of this invention include, for example, those caused by hepatitis B viruses.

Flaviviridae infections that may be prevented or treated using the methods of this invention include, for example, those caused by hepatitis C virus, yellow fever virus, dengue virus and tick-borne encephalitis viruses.

Togaviridae infections that may be prevented or treated using the methods of this invention include, for example, those caused by rubella virus.

Rhabdoviridae infections that may be prevented or treated using the methods of this invention include, for example, those caused by rabies virus and vesicular stomatitis virus.

Poxviridae infections that may be prevented or treated using the methods of this invention include, for example, those caused by vertebrate and avian poxviruses and vaccinia viruses.

Arenaviridae infections that may be prevented or treated using the methods of this invention include, for example, those caused by the arenaviruses.

Coronaviridae infections that may be prevented or treated using the methods of this invention include, for example, those caused by the coronaviruses.

Bunyaviridae infections that may be prevented or treated using the methods of this invention include, for example, those caused by the hantaviruses.

Filoviridae infections that may be prevented or treated using the methods of this invention include, for example, those caused by Marburg, Reston and Ebola viruses.

Preferably, the enveloped viral infection to be treated or prevented is one wherein the virus is from the genera Retroviridae, Herpesviridae, Orthomyxoviridae, Paramyxoviridae, Hepadnaviridae, Flaviviridae, or Rhabdoviridae. More preferably, the virus is type 1 or type 2 human immunodeficiency virus, type 1 or type 2 herpes simplex virus, varicella zoster virus, Epstein-Barr virus, cytomegalovirus, influenza type A, B, or C virus, respiratory scincytial virus, mumps virus, hepatitis B virus, hepatitis C virus, encephalitis virus, rabies virus, or dengue fever-inducing virus. Most preferably, the virus is type 1 or type 2 human immunodeficiency virus or type 1 or type 2 herpes simplex virus.

Important examples of parasitic targets for which carbohydrate crosslinked glycoprotein crystal based vaccines include those in the kingdom Protozoa.

Protozoa infections that may be prevented or treated using the methods of this invention include those caused by representatives of the Sarcomastigophora (containing flagellates and amebas); Apicomplexa (containing the sporozoans) and Ciliophora (containing the ciliates).

Sarcomastigophora infections that may be prevented or treated using the methods of this invention include, for example, those caused by *Trypanosoma cruzi, Toxoplasma gondii, Leishmania major.*

Apicomplexa infections that may be prevented or treated using the methods of this invention include, for example, those caused by *Plasmodium falciparum.*

Ciliophora infections that may be prevented or treated using the methods of this invention include, for example, those caused by *Balantidium coli.*

Parasitic worm infections for which vaccines may be effective include, for example, those caused by the classes Cestoda (tapeworms) and Trematoda (flukes).

According to one embodiment of this invention, the use of dried carbohydrate crosslinked glycoprotein crystals permits routine handling and storage of these materials prior to use (dry storage at room temperature or above without refrigeration, for extended periods of time). The ability to transport the carbohydrate crosslinked glycoprotein crystals at ambient temperatures without denaturation of the glycoprotein advantageously overcomes the problem of inadequate refrigeration of vaccines often encountered during global distribution of vaccines.

Dried carbohydrate crosslinked glycoprotein crystals also allow for routine formulation by direct addition of adjuvants and immune modifying cytokines such as Type I interferon, immune interferon, tumor necrosis factor, interleukin-1, interleukin-2, interleukin-3, interleukin-4, interleukin-5, interleukin-6, interleukin-8, interleukin-10, interleukin-12, colony stimulating factors and other immune modifiers.

Any conventional pharmaceutically acceptable carrier or adjuvant may be combined with the carbohydrate crosslinked glycoprotein crystals of this invention. These carriers and adjuvants include, for example, Freund's complete and incomplete, bacterial lipolysaccarides, cholera toxin, mono and di-phosphoryl lipid A, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium, trisilicate, polyvinyl pyrrolidone, cellulose-based substances and polyethylene glycol. Adjuvants for topical or gel base forms may be selected from the group consisting of sodium carboxymethylcellulose, polyacrylates, polyoxyethylene-polyoxpropylene-block polymers, polyethylene glycol, natural and synthetic gum bases, and wood wax alcohols.

Formulations may include any excipient or carrier which may be added to carbohydrate crosslinked glycoprotein crystals or pharmaceutical salts thereof, without affecting their biological activity.

According to another embodiment, this invention provides a method for treating or preventing an enveloped virus infection in a patient comprising the step of administering to said patient a composition comprising: an amount of a carbohydrate crosslinked glycoprotein that is also an immune response modifier or antibody, sufficient to reduce or prevent viral replication in said patient via modification of patients immune response or direct interaction with said virus.

A carbohydrate crosslinked glycoprotein crystal or a combination of carbohydrate crosslinked glycoprotein crystals can be used as a component of a sensor, referred to as a biosensor, useful for detecting and/or measuring an analyte of interest in a fluid, such as body fluid (e.g., blood, urine), chemical and laboratory reaction media, organic media, water, culture medium and beverages. In some instances, the fluid in question can be a gas, as in an alcohol breath analyzer [E. Barzana, A. Klibanov and M. Karell, *NASA Tech Briefs*, 13, p. 104, (1989)]. In this application an appropriately-selected carbohydrate crosslinked glycoprotein crystal is brought into contact with a fluid to be analyzed for the analyte of interest. The analyte of interest can be measured directly (e.g., blood glucose) or indirectly (e.g., by detecting or measuring a substance which is a reactant (product or substrate) in a reaction in which the analyte of interest participates). In either case, the carbohydrate crosslinked glycoprotein crystal is able to act upon the analyte or the substance which is a reactant in a reaction in which the analyte also participates. The activity of the enzyme results in a detectable change (e.g., change in pH, production of light, heat, change in electrical potential) which is detected and/or quantified by an appropriate detecting means (e.g., pH electrode, light or heat sensing device, means for measuring electrical change) [J. Janette, et al., Anal. Chem., 62, pp. 33R–44R (1990)]. Any means useful for detecting the change resulting from the enzyme-catalyzed method can be used. A biosensor of the present invention includes a carbohydrate crosslinked glycoprotein crystal or a combination of carbohydrate crosslinked glycoprotein crystals and a retaining means for the carbohydrate crosslinked glycoprotein crystal which allows contact between the carbohydrate crosslinked glycoprotein crystal (s) and the analyte of interest or the substance in the fluid which is a reactant in the reaction in which the analyte of interest participates.

The carbohydrate crosslinked glycoprotein crystals of this invention may be used in any of a number of chemical processes. Such processes include industrial and research-scale processes, such as organic synthesis of specialty chemicals and pharmaceuticals. Enzymatic conversion processes include oxidations, reductions, additions, including esterifications and transesterifications, hydrolyses, eliminations, rearrangements, and asymmetric conversions, including stereoselective, stereospecific and regioselective reactions.

Carbohydrate crosslinked glycoprotein crystals according to this invention may also be used in various environmental applications. They may be used in place of conventional soluble or immobilized proteins for environmental purposes, such wide area decontamination of environmental hazards.

Alternatively, the carbohydrate crosslinked glycoprotein crystals of this invention may be used in cleaning agents, selected from the group consisting of detergents, such as powdered detergents and liquid detergents, bleaches, household cleaners, hard surface cleaners, industrial cleaners and carpet and upholstery shampoos.

Cleaning agents containing carbohydrate crosslinked glycoprotein crystals according to the present invention may also comprise compounds conventionally included in such agents. See, for example, *Soaps and Detergents, A Theoretical and Practical Review*, Louis Spitz (Ed.), AOCS Press (Champlain, Ill.) (1996). Such compounds include anionic, non-ionic, cationic or zwitterionic surfactants, or mixtures thereof.

Anionic surfactants are exemplified by alkyl sulfates, alkyl ether sulfates, alkyl sulfonates, alkylaryl sulfonates, olefin sulfonates, alkyl ether phosphates, alkyl ether phosphates, fatty acid salts, soaps, isothionates and sulfonated unsaturated esters and acids.

Non-ionic surfactants are exemplified by products of condensation of an organic aliphatic or alkyl aromatic hydrophobic compound with an alkylene oxide, alkyl polyglucosides and sugar esters.

Cationic surfactants are exemplified by quarternary ammonium salts of tertiary alkyl amines, amino amides, amino esters or imidazolines containing al least one long chain ($C_8$–$C_{22}$) aliphatic group or an alkyl-aryl group, wherein alkyl comprises about 4 to 12 carbon atoms and aryl is preferably a phenylene group.

Zwitterionic surfactants are exemplified by derivatives of quarternary ammonium, quarternary phosphonium or tertiary sulfonium compounds, derivatives of secondary and tertiary amines and derivatives of heterocyclic secondary and tertiary amines.

Carbohydrate crosslinked glycoprotein crystals according to this invention may also be used as ingredients in personal care compositions, including cosmetics, such as creams, lotions, emulsions, foams, washes, compacts, gels, mousses, slurries, powders, sprays, pastes, ointments, salves, balms, drops, shampoos and sunscreens. In topical creams and lotions, for example, they may be used as humectants or for skin protection, softening, bleaching, cleaning, deproteinization, lipid removal, moisturizing, decoloration, coloration or detoxification. They may also be used as anti-oxidants in cosmetics.

An alternate embodiment of the present invention includes protein delivery systems comprising carbohydrate crosslinked glycoprotein crystals. Such a system may be used to deliver glycoproteins such as those included in personal care products, such as cosmetics, pharmaceuticals, veterinary compositions, vaccines, foods, feeds, diagnostics, cleaning agents, such as detergents, and formulations for decontamination. Glycoprotein delivery systems of this invention, which may be formulations or devices, such as implantable devices, may be microparticulate glycoprotein delivery systems.

In such systems, as well as in other embodiments of the present invention, carbohydrate crosslinked glycoprotein crystals have a longest dimension between about 0.01 $\mu$m and about 500 $\mu$m, alternatively between about 0.1 $\mu$m and about 50 $\mu$m. The crosslinked glycoprotein crystal components may have a shape selected from the group consisting of: spheres, needles, rods, plates, such as hexagons and squares, rhomboids, cubes, bipyramids and prisms. Advantageously, the crosslinked crystal form of the glycoproteins of this invention allow loading of up to between about 50% and about 90% protein per unit of weight.

According to one embodiment of this invention, carbohydrate crosslinked glycoprotein crystals are characterized by stability and integrity under elution conditions used in separations, particularly chromatography elution conditions, as compared with the soluble uncrosslinked form of the protein that is crystallized to form the glycoprotein crystals that are crosslinked. Alternatively, carbohydrate crosslinked glycoprotein crystals are characterized by stability and integrity in the presence of a solvent contained in the sample to be separated, as compared with the soluble uncrosslinked form of the glycoprotein that is crystallized to form the glycoprotein crystals that are crosslinked.

The carbohydrate crosslinked glycoprotein crystals may be used for high throughput screening in combinatorial chemistry, where large libraries may be screened for specific interaction with the glycoprotein component of the crystals.

An advantage of this invention is that chromatographic separations may be carried out in the presence of an aqueous solvent, an organic solvent, or an aqueous-organic solvent mixture.

In order that this invention may be better understood, the following examples are set forth. These examples are for the purpose of illustration only and are not to be construed as limiting the scope of the invention in any manner.

EXAMPLES

Example 1

Preparation of Glucose Oxidase Crystals

We prepared crystals of glucose oxidase as follows. First, the glycoprotein was purified by anion exchange chromatography and then the crystallization parameters were optimized.

A. Preparative Chromatography of Glucose Oxidase

One volume of 50 ml of crude glucose oxidase "GO" (Novo Nordisk Bioindustrials, Franklinton, N. C.) was diluted with 4 volumes, 200 ml, of 25 mM Na-acetate at a pH of 4.5. The solution was diafiltered with Fresenius F 40 hollow fiber ultrafilter to equilibrium with the buffer. Glycoprotein concentration was expressed as ultraviolet absorbance at wavelength 280 nm, and abbreviated as A 280 nm. The A 280 nm of a sample is reproducible and is directly proportional to the glucose oxidase concentration when the enzyme sample is pure, i.e. contains only glucose oxidase glycoprotein. After diafiltration, the volume was 265 ml with an A 280 nm equal to 18.9. Then 160 ml of the filtered solution was slowly pumped onto a Pharmacia XK 16 chromatography column with a 16 mm inner diameter, 20 cm length and 14 cm bed height packed with 28 ml of Q-sepharose. The column was washed with 58 ml of the 25 mM Na-Acetate pH 4.5 running buffer prior to elution. Glucose oxidase was eluted with 80 mM NaCl and stored at 4° C. for use in crystallization experiments. Glucose oxidase purchased from Sigma Chemical Co., St. Louis, Mo., was also purified for use in crystallization experiments.

B. Optimization of Crystal Formation 1.0 Effect of Polyethylene Glycol Molecular Size We analyzed the effect of polyethylene glycol "PEG" molecular size on crystal formation in small scale microdiffusion experiments using the Hanging Drop method. In the Hanging Drop method, the drop hangs with surface tension on a cover slide over a chamber filled with crystallizing media. The drop consists of 5 µl of enzyme solution sample plus 5 µl of the chamber solution. The chamber is sealed tightly with the cover slide (hanging drop inside). Diffusion concentrates the drop slowly to a volume of 5 µl and allows supersaturation of the glycoprotein. The volume pipetted into the chamber is typically 400–500 µl.

The following molecular sizes were evaluated; PEG 400, 600, 1000, 4000, 6000, or 8000 at four different concentrations each. The PEG 400 varied from 20–50% final concentration. The PEG 600 varied from 9–20% concentration. The PEG 1000 varied from 8–15% final concentration. The PEG 4000 varied from 7–13% final concentration. The PEG 6000 varied from 6–10% final concentration. The PEG 8000 varied from 4–8% final concentration. The pH was kept constant at 5.0 and citric acid concentration varied from 0.1 M to 0.2 M. The initial glycoprotein concentration was A280 of 14.4 and increased to A280 of 28.8, while the lithium chloride (LiCl) concentration varied from 1 to 2 Molar. We previously determined that an A 280 nm=1.0 for glucose oxidase indicates that the concentration of glucose oxidase is 0.714 mg/ml.

Large crystals of glucose oxidase were produced with PEG 600, 1000, 4000, and 6000. The amorphous precipitate form was favored with the high LiCl concentration, making complete crystallization difficult. We next evaluated the effects of LiCl and pH on crystal formation.

2.0 Effect of pH and LiCl

The pH was then varied between 5.0, 5.5 and 6.0, to determine the optimum pH for glycoprotein crystallization. Crystallization was carried out within this range in either the presence or absence of 1.0 M LiCl, that was added gradually by hanging drop. The maximum protein concentration reached an A280 of 24.2 or 24.5 and the PEG 6000 varied from 10–20% final concentration. The entire experiment was carried out with both Sigma Chemical Co. [SI] and Novo Nordisk [NO] glucose oxidase from Aspergillus niger. Crystals could be obtained without LiCl, in solutions containing between 10 and 20% PEG.

3.0 Effect of PEG Size without LiCl

We next evaluated the effect of removing LiCl on crystal formation using four different molecular sizes of PEG: PEG 200, 400, 600, 1000, 4000, or 6000, at four concentrations. The PEG 200 varied from 15–30% final concentration. The PEG 400 varied from 10–25% final concentration. The PEG 600 varied from 8–20% final concentration. The PEG 1000 varied from 5–15% final concentration. The PEG 4000 varied from 5–13% final concentration. The PEG 6000 varied from 5–10% final concentration. The pH was kept constant at 5.0 and the Na-citrate buffer was 0.1 M. The initial glycoprotein concentration was A280 of 13.1 and increased to A280 of 26.2.

As a result of the small scale hanging drop microdiffusion studies, we determined that optimal crystals were obtained using either 20% PEG 4000 or PEG 6000, in the absence of LiCl.

4.0 Batch Crystallization

We carried out batch crystallizations of glucose oxidase using reagents prepared at their final concentrations and incubation under the specified conditions. Small batches having different PEG 4000 concentrations were prepared in 1.5 ml Eppendorf tubes. The samples were buffered in 0.1 M Na-Acetate at pH 5.0 and rocked at room temperature. The results are shown in Table 1 below, in which "C" designates crystals, C* indicates the most uniform crystals obtained and "L" designates liquid phase separation.

TABLE 1

| PEG % | 50% PEG 4000 in buffer | Enzyme SI in buffer µl | Initial A280 | Soluble A280 after 3 days | results after 3 days |
|---|---|---|---|---|---|
| 15 | 300 | 700 | 27.7 | 18.4 | LC |
| 16 | 320 | 680 | 26.9 | 10.1 | C |
| 17 | 340 | 660 | 26.1 | 5.2 | C |
| 18 | 360 | 640 | 25.3 | 3.3 | C |
| 19 | 380 | 620 | 24.6 | 2.0 | C* |
| 20 | 400 | 600 | 23.8 | 1.6 | C* |

Crystallization conditions in the samples having 16% or higher PEG concentration produced very good crystals.

5.0 Addition of Organic Solvents

The addition of water miscible organic solvent to a solution containing glycoprotein, PEG and buffer reduces the viscosity and the amorphous gel precipitation. Therefore, concentrations of PEG were chosen at the low end of the effective crystallization range. Both 15% and 17% PEG 6000 and, in a few cases, PEG 4000 we re used in batch crystallizations at room temperature.

A stock solution of 1.5 g of glucose oxidase in 50 ml of 0.2 M Na-acetate at pH 5.0 was prepared. The A280 of this solution was 46. The crystallizations were begun by mixing 0.5 ml of protein with 0.5 ml of the PEG-solvent mixture, which had twice the final concentration indicated. The final PEG concentration was 15% in each experiment. The solvents were used at final concentrations of 5, 10 or 150. The results are shown in Tables 2 and 3 below, in which "MPD" designates 2-methyl-2,4-pentanediol, "A" designates amorphous, "C" designates crystals, "Cg" designates granule-like crystals and "L" designates liquid phase separation.

TABLE 2

Effect of Solvents in 15% PEG 6000 at Room Temperature
Constant parameters
Sample SI, A280 = 23
Temp = RT
Precipitant = 15% (V/V) PEG 6000

| Exp | Solvent | Conc (V/V) | Supernat A280 at 6 days | Microscopy Results after 5 days |
|---|---|---|---|---|
| 1 | Ethanol | 5% | 5.05 | G |
| 2 | Ethanol | 10% | 1.84 | C |
| 3 | Ethanol | 15% | 0.95 | C |
| 4 | 2-Propanol | 5% | 0.87 | C |
| 5 | 2-Propanol | 10% | 2.25 | Cg |
| 6 | 2-Propanol | 15% | 4.64 | G |
| 7 | Acetone | 5% | * | Cg |
| 8 | Acetone | 10% | * | Cg |
| 9 | Acetone | 15% | * | Cg |
| 10 | MPD | 5% | 10.07 | Cg |
| 11 | MPD | 10% | 11.82 | Cg |
| 12 | MPD | 15% | 12.19 | Cg |
| 13 | Ethylene glycol | 5% | 5.37 | Cg |
| 14 | Ethylene glycol | 10% | 2.69 | N |
| 15 | Ethylene glycol | 15% | 1.68 | C |
| 16 | Water | | 9.16 | Cg |

Water miscible organic solvents greatly improved the crystallization, particularly ethanol and 2-propanol. The other combinations produced only granular sticky gel precipitates. The reference sample with PEG alone did not yield any crystals.

TABLE 3

Effect of Solvents in 17% PEG 6000 at Room Temperature
Constant parameters
Sample SI GO
A280 = 23 Temp = RT
Precipitant = 17% (V/V) PEG 6000

| Exp. | Solvent | Conc (V/V) | Supernat A280 at 6 days | Microscopy Results after 5 days |
|---|---|---|---|---|
| 17 | EtOH | 5% | 1.58 | C |
| 18 | EtOH | 10% | 0.74 | C |
| 19 | EtOH | 15% | 0.67 | C |
| 20 | 2-Propanol | 5% | 1.54 | C |
| 21 | 2-Propanol | 10% | 1.05 | C |
| 22 | 2-Propanol | 15% | 0.72 | Cg |
| 23 | Acetone | 5% | * | C |
| 24 | Acetone | 10% | * | C |
| 25 | Acetone | 15% | * | C |
| 26 | MPD | 5% | 2.01 | N |
| 27 | MPD | 10% | 1.25 | N |
| 28 | MPD | 15% | 1.11 | Cg |
| 29 | Ethylene glycol | 5% | 4.31 | Cg |
| 30 | Ethylene glycol | 10% | 5.21 | Cg |
| 31 | Ethylene glycol | 15% | 5.8 | Cg |
| 32 | Water | | 4.13 | Cg |

This series of examples produced more complete crystallization than the previous set (Table 2). Three of the solvents induced good crystal formation namely, ethanol, 2-propanol, and acetone. On microscopic analysis, we determined that the crystals were better and the crystallization process more complete than in the previous set of examples.

6.0 The Effect of Solvents at 4° C.

The samples were mixed as in the previous example using 15% PEG 6000 and rocked in the refrigerator at 4° C. The results are shown in Table 4 below, in which "C" designates crystals, and "Cg" designates granule like crystals.

TABLE 4

Effect of Solvents in 15% PEG 6000 at 4° C.
Constant parameters Sample = SI GO
A280 = 23, Temp = 4° C.
Precipitant = 15% (V/V) PEG 6000

| Exp | Solvent | Conc (V/V) | Supernat A280 at 6 days | Microscopy Results after 5 days |
|---|---|---|---|---|
| 33 | EtOH | 5% | 3.27 | CgC |
| 34 | EtOH | 10% | 1.56 | CgC |
| 35 | EtOH | 15% | 1.1 | C |
| 36 | 2-Propanol | 5% | 0.71 | Cg |
| 37 | 2-Propanol | 10% | 1.65 | C |
| 38 | 2-Propanol | 15% | 2.54 | CgC |
| 39 | Acetone | 5% | * | C |
| 40 | Acetone | 10% | * | C |
| 41 | Acetone | 15% | * | Cg |
| 42 | MPD | 5% | 4 | Cg |
| 43 | MPD | 10% | 2.28 | Cg |
| 44 | MPD | 15% | 1.05 | Cg |
| 45 | Ethylene glycol | 5% | 7.3 | Cg |
| 46 | Ethylene glycol | 10% | 7.49 | Cg |
| 47 | Ethylene glycol | 15% | 8.09 | Cg |
| 48 | Water | | 6.2 | Cg |

The reactions containing ethanol, 2-propanol and acetone all produced good crystals. The result was greatly improved over that obtained by incubation at room temperature.

The crystallization shown below in Table 5 was performed as described for Table 3, except that the samples were incubated and rocked at 4° C. In Table 5, "C" designates crystals, and "Cg" designates crystal-like granules.

TABLE 8

Effect of Solvents in 17% PEG 6000 at 4° C.
Constant parameters Sample = SI GO
A280 = 23, Temp = 4° C.
Precipitant = 17% (V/V) PEG 6000

| Exp | Solvent | Conc (V/V) | Supernat A280 at 6 days | Microscopy Results after 5 days |
|---|---|---|---|---|
| 49 | EtOH | 5% | 1.48 | CgC |
| 50 | EtOH | 10% | 1 | CgC |
| 51 | EtOH | 15% | 0.8 | Cg |
| 52 | 2-Propanol | 5% | 1.27 | CgC |
| 53 | 2-Propanol | 10% | 0.88 | CgC |
| 54 | 2-Propanol | 15% | 0.75 | Cg |
| 55 | Acetone | 5% | * | C |
| 56 | Acetone | 10% | * | CgC |
| 57 | Acetone | 15% | * | Cg |
| 58 | MPD | 5% | 1.39 | CgC |
| 59 | MPD | 10% | 1.18 | CgC |
| 60 | MPD | 15% | 0.94 | Cg |
| 61 | Ethylene glycol | 5% | 2.89 | Cg |
| 62 | Ethylene glycol | 10% | 3.07 | Cg |
| 63 | Ethylene glycol | 15% | 4.26 | Cg |
| 64 | Water | | 2.59 | Cg |

The samples containing the solvents ethanol, 2-propanol and acetone produced good crystals. However, the results were not improved over that are obtained at room temperature. One difference was that the sample with MPD produced crystals, a result not obtained at room temperature.

In summary, the addition of organic solvents resulted in dramatic improvements in crystal quality and quantity and also reduced the amorphous precipitate formation. Refrigeration seemed to improve the situation even further. Ethanol and 2-propanol were selected for additional optimization.

7.0 Optimization of PEG 6000 and 2-Propanol at Reduced Protein Concentration

A stock solution of 50% PEG 6000 was prepared in 0.1 M Na-acetate at pH 5.0. The glucose oxidase stock solution was prepared with 1.5 g of Sigma Chemical Co. glycoprotein in 50 ml of 0.2 M Na-acetate. The A280 of the glucose oxidase solution was 46. 2-Propanol was used as 100%. These solutions were mixed to produce the various final combinations: Crystals were observed only in solutions with 15% PEG and 10 or 15% 2-propanol. All other samples had amorphous precipitate or gel granules. The soluble protein level declined to less than 10% of the initial value in the samples with crystals, thus indicating that 90% or more protein was either crystallized or precipitated.

The above crystallization conditions were used with twice the input protein level or A280 of 20. Under these conditions, crystals were observed only in solutions having 15% PEG and either 5 or 10% 2-propanol. The other samples had only amorphous precipitate. Under the conditions that produced crystals, the A280 value of the supernatant indicates that 83–93% of the protein was in the form of crystals and precipitate.

The same conditions discussed above were employed with PEG 4000 instead of PEG 6000. The effect of PEG 4000 was evaluated with 2-propanol concentrations of 5, 10, and 15%. A stock solution of 50% PEG 4000 was prepared and the solutions were mixed to achieve the same conditions as discussed above. This example was carried out at room temperature, in 0.1 M Na-acetate.

In the first example, 10 mg/ml glycoprotein was used. The samples having 15% PEG 4000 and 10 or 15% 2-propanol were crystallized. All other combinations produced only amorphous precipitate. The crystallized samples showed that 85–92% of protein converted into solid phase including crystals and precipitate. In general, the results were very similar to those achieved using PEG 6000.

The next example used a glycoprotein content of equal to an A280 of 20 in the conditions discussed above. Only the sample having 15% PEG 4000 and 10% 2-propanol produced crystals. The other samples had only amorphous precipitate. In the sample with crystals, 88% of the glycoprotein was in the solid phase.

In summary, PEG 4000 and PEG 6000 both are suitable for inducing glycoprotein crystal formation. The combination of 15% PEG 4000 or PEG 6000 and 10–15% 2-propanol, using relatively low protein levels, was remarkably effective in producing good quality glycoprotein crystals. By microscopy, all the crystallized samples had initially lumps of glassy gel precipitate prior to crystal growth. It appeared as though the crystals were growing out of the surface of the gel particles.

8.0 Optimization of PEG 6000 and Ethanol at Reduced Protein Concentration

The potential of ethanol in combination with PEG 6000 as glycoprotein precipitants was evaluated. A total of 2.5 g of glucose oxidase glycoprotein from Sigma Chemical Co. was dissolved in 25 ml water and the solution was filtered through a 0.2 µm membrane. This enzyme stock solution had an A280 of 139.4. A 50% PEG 6000 stock solution was prepared in 0.1 M Na-acetate at pH 5.0. Batch crystallization samples were prepared in Eppendorf tubes by mixing the following reagents:

1. 0.1 ml of glycoprotein stock solution (each batch final A280=13.9),
2. sufficient PEG 6000 stock solution to reach the target concentration of 0 to 19%,
3. sufficient 100% ethanol to get to the target concentration of 0–21%; and
4. 0.1 M Na-acetate to reach the final volume of 1.0 ml.

The samples were rocked at room temperature and inspected by microscopy 1, 3 and 8 days after mixing. Finally, the samples were centrifuged at 10,000 RPM for 15 minutes and the soluble protein in supernatant was measured as A280 nm.

Glycoprotein crystals were produced under conditions where the PEG 6000 concentration was 15 or 17% and the ethanol concentration was 5–21%. The best ethanol conditions for glycoprotein crystallization were between 11–17%. PEG 6000 alone or ethanol alone did not induce crystal formation. Typical soluble protein levels in the samples that were well crystallized was around an A280 of 1.0. Thus, in most of the crystallized samples greater than 90% of the protein was in the solid phase, crystals and precipitate. Under the best conditions, crystallization occurred overnight.

9.0 Preparative Batch Crystallizations with PEG 6000 and 2-propanol

Once the total volume of the batches increased from 1 ml to 5 ml, gel formation became somewhat problematic. The best conditions for crystal formation without gel formation were re-evaluated. Four different PEG 6000 concentrations were screened with 2-propanol from 3–20% (V/V) in 0.1 M Na-acetate. The 5.0 ml batch samples were prepared and rocked at 6° C., and evaluated by microscopy after days 1, 2, and 8. The results are shown below in Table 6, in which "A" designates amorphous, "C" designates crystals, "G" designates granule gel, "N" designates no phase separation and "L" designates liquid phase separation.

TABLE 6

Optimization of conditions for 5.0 ml preparative scale crystallizations

| | Precipitants | | | Microscopy Results After | | | |
|---|---|---|---|---|---|---|---|
| Exp | 2-propanol Conc (V/V) | PEG 6000 Conc (W/V) | A 280 at 9 days | 0 | 1 | 3 | 8 |
| | | | | | | days | |
| 1 | 10% | 6% | 18.3 | N | C | — | C |
| 2 | 12% | 6% | 17.3 | N | LC | — | C |
| 3 | 14% | 6% | 15.9 | N | L | — | C |
| 4 | 16% | 6% | 14.4 | N | L | — | C |
| 5 | 18% | 6% | 10.4 | N | C | N | C |
| 6 | 20% | 6% | 8.0 | N | GC | C | CG |
| 7 | 8% | 9% | 12.9 | N | C | — | C |
| 8 | 10% | 9% | 8.8 | N | L | C | CG |
| 9 | 12% | 9% | 6.8 | A | CG | C | C |
| 10 | 14% | 9% | 6.4 | A | CG | C | CG |
| 11 | 16% | 9% | 4.9 | A | AC | C | C |
| 12 | 18% | 9% | 4.5 | A | CG | C | C |
| 13 | 6% | 10% | 9.4 | A | L | C | CG |
| 14 | 8% | 10% | 7.0 | A | CG | C | CG |
| 15 | 10% | 10% | 5.9 | A | CG | C | CG |
| 16 | 12% | 10% | 5.4 | A | CG | C | CG |
| 17 | 14% | 10% | 4.7 | A | LCG | C | C |
| 18 | 3% | 12% | 6.8 | A | LC | C | CG |
| 19 | 4% | 12% | 6.2 | A | CG | C | C |
| 20 | 5% | 12% | 5.7 | A | CG | C | C |

As shown in Table 6, the combination of 9% PEG 6000 and 12% 2-propanol produced rapid crystal formation without gel.

SUMMARY

As a result of these studies, we believe that the conditions for crystallization of glucose oxidase fall generally in the range of 7 to 17% PEG 4000 or 6000, 8 to 20% 2-propanol or ethanol, and buffer to adjust the pH to between 3 and 6. It should be understood, however, that many sets of experimental conditions within and near this range can produce satisfactory results for the crystallization of glucose oxidase and other glycoproteins. Those of skill in the art will appreciate that the precise conditions which efficiently produce crystals of the desired size and quality, will vary due to differences in experimental conditions, such as protein and reagent purity, rates of stirring, shear force effects, and carbohydrate content.

Example 2

Large Scale Crystallization of Glucose Oxidase

Based on the optimization procedures outlined in Example 1, we determined preferred conditions for preparative scale crystallization of glucose oxidase. Preparative scale crystallization generally involves 100 to 900 mls of glycoprotein. The procedures are exemplified below:

A. Crystallization at Constant pH Without Seed

Glucose oxidase was diafiltered in water and concentrated to an A 280 nm of between 5 and 15. The glucose oxidase concentrate was mixed (1:1) with one volume of the crystallizing reagent containing 18% PEG 6000, 32% 2-propanol in 0.2 M Na-Acetate at pH 5.0. After mixing, the solution was cooled to 6° C. The glucose oxidase crystallization solution was stirred for 24 hours at 100 rpm with a propeller stirrer. During this time, the crystals formed gradually.

B. Crystallization at Constant pH With Seed Crystals

This method is similar to the "crystallization at constant pH without seed crystals" method described above, except that seed crystals from previous batches were added after mixing the glycoprotein concentrate and crystallizing reagent. Crystallization occurred more rapidly by this method and there were many crystals after 1 hr of mixing.

C. Crystallization by Gradual pH Reduction

This method was carried out at a higher pH than the two examples shown above. The supersaturation of the solution was slowly increased by gradually lowering the pH to the point of lowest glucose oxidase solubility at pH 4.5.

The initial crystallization mixture included 35 ml of glucose oxidase stock solution with A 280 nm of 103, 337 ml water, 400 ml crystallizing reagent. The crystallizing reagent contained 180 g PEG 6000, 320 ml 2-propanol, 0.145 moles Na-Acetate and diluted to 1000 ml. The initial pH is usually between 6.5 and 7.0. The initial pH does not allow crystallization.

Crystallization was initiated by pumping 28.4 ml of 1 M acetic acid into the batch with a flow rate of 2.2 ml/hr. The mixture was slowly cooled to 5° C. over 12 hours. The final pH was 4.5 and was stirred at 100 rpm.

Glucose oxidase crystallized during the first 24 hours and formed crystals of between 10 to 15 µm. This method reproducibly produced the optimal and most uniform crystals.

Example 3

Carbohydrate Crosslinking of Glucose Oxidase Crystals

We then crosslinked the glucose oxidase crystals prepared in Example 1 as follows. More particularly, we crosslinked the crystals by first using oxidation of the carbohydrate, followed by crosslinking with a diamine compound and then finally reduction of the imine. The reduction step is one variable which can be used to control the relative insolubility or rate of dissolution of the carbohydrate crosslinked glycoprotein crystals. If controlled dissolution carbohydrate crosslinked glycoprotein crystals are the goal, then the reduction step can be left out. However, if insoluble carbohydrate crosslinked glycoprotein crystals are desirous then the reduction step should be included. This series of reactions causes the carbohydrate moieties within and between protein molecules to become covalently crosslinked, thus stabilizing the crystalline form of the glycoprotein. According to an alternate embodiment of this invention, carbohydrate crosslinking may be combined with other carbohydrate crosslinking reactions or reactions that crosslink through amino acid side chain functional groups of the amino acid residues of the protein backbone. It should be understood that he particular combinations of these reactions determine the level of protein activity within the crystal, the rate of dissolution, the preservation of antigenic and immunogenic epitopes and the resistance to proteases, organic solvents, extremes of temperature and pH.

A. Crosslinking of Glucose Oxidase Through the Attached Carbohydrate 1.0 Oxidation of Carbohydrates Crystalline glucose oxidase, 102 mg, as prepared in Example 2, using method B was suspended in crystallization buffer consisting of 9% PEG 6000, 12% 2-propanol, 0.1 M Na-acetate at pH 5.0 at 6° C. Then 68 to 586 mg of sodium periodate ($NaIO_4$) was added per gram of glycoprotein crystal. All samples were protected from the light throughout the oxidation period. To carry out the oxidation, samples 1–4, shown in Table 7, were rocked for 2 hours at room temperature, samples 5 and 6, were rocked overnight at 4° C. The crystals were centrifuged at 10,000 RPM for 10 minutes and then washed three times with crystallization buffer. Controlled dissolution activity of the crystals, shown in Table 7, was measured by separating them by filtration after 30 minutes of titration and measuring the enzyme activity from the filtrate. In Table 7, the dissolved activity is presented as a percentage of the total activity after 30 minutes of titration.

2.0 Reaction with Diamine

The crystals were dispersed in a diamine reagent solution consisting of 0.25 M 1.8-diaminooctane, 9% PEG 6000, 16% 2-propanol in 0.1 M Na-acetate at pH 5.0. The reaction was allowed to proceed overnight at room temperature.

3.0 Reduction of Imine Compound

The amine reaction was terminated by addition of 760 mg of solid $NaCNBH_3$ per gram of protein directly on the reaction mixture and incubated 90 minutes at room temperature. Crystals were centrifuged and washed four times with 2 mM sodium phosphate, pH 7.0.

TABLE 7

Protein activity of carbohydrate crosslinked glycoprotein crystals

| Sample No. | $NaIO_4$ mg/g GO | Titrimetric activity U/µg | | Activity of filtrate U/µg | Controlled dissolut. activity % of total |
|---|---|---|---|---|---|
| | | Titr. 10 min | Titr. 30 min | | |
| 1. | 69 | 135 | 206 | 152 | 74 |
| 2. | 147 | 85 | 102 | 74 | 72 |
| 3. | 284 | 99 | 155 | 108 | 70 |
| 4. | 588 | 114 | 164 | 98 | 60 |
| 5. | 147 | 180 | 271 | — | — |
| 6. | 441 | 123 | 131 | 88 | 67 |

4.0 Measurement of Glycoprotein Activity

The glycoprotein enzyme known as glucose oxidase, also known as β-D-glucose 1-oxidoreductase (enzyme commission number 1.1.3.4) catalyzes the oxidation of β-D-glucose to D-glucono-1,5-lactone and hydrogen peroxide ($H_2O_2$). The reaction consumes one mole of oxygen per mole of glucose. The D-glucono-1,5-lactone subsequently hydrolyses to gluconic acid and the appearance of which in solution may be used to measure enzyme activity, as described below.

4.1 Titration of Protein Activity

The activity of the carbohydrate crosslinked glucose oxidase crystals was measured by titrating the production of gluconic acid. The analysis was performed in a 1000 ml reaction vessel which was immersed in 30° C. temperature controlled water bath. The approximate diameter of the liquid was 95 mm and depth 60 mm. The batch was agitated with overhead propeller stirrer equipped with digital rpm indicator. The stirrer was a 55 mm diameter 6 blade propeller. Air was dispersed in the batch through two pieces of 13 mm×13 mm Pyrex No. 1 glass sinter beads. Air was pumped with Watson Marlow 603S peristaltic pump using 9.5 mm internal diameter pump hose. The process was controlled with Radiometer PHM 290 titrator. The results were collected with a computer which was connected to the titrator. The titrator control settings were the following:

| Point | 1 min |
|---|---|
| Time constant | 5.0 sec |
| Gain | 0.01 |
| Set point | pH 6.0, if not otherwise stated. |

Specifics of the Procedure Include:
1. Process volume was 400 ml in the start of titration.
2. Glucose 100 g/l in deionized water, no buffer added
3. carbohydrate crosslinked glucose oxidase crystals as dry substance in the batch
4. Catalase 0.1 ml (500 units), Genencor CAT HP L5000
5. Stirring 1000 rpm
6. Aeration 2.4 1/min.
7. Temperature 30° C.
8. The titration was made with 1 M or 10 M NaOH.
9. Set point pH 6.0.

The total quantity of glucose was 0.222 moles in the standard analysis; thus the total consumption of 10 M NaOH was 22.2 ml, if the reaction was allowed to proceed to 100% conversion. The standard conditions were used if not otherwise stated.

This example demonstrates carbohydrate crosslinking of glycoproteins. The crystals subjected to the oxidation reaction with diamine and reduction reactions were all active and relatively insoluble during extensive washing.

By virtue of their controlled dissolution protein activity, carbohydrate crosslinked crystals of glucose oxidase produced using this method of crosslinking would be preferred in the preparation of crosslinked glycoproteins from viruses, parasites, tumors and cytokines, as well as other immune modifying glycoproteins for use in vaccines and immunotherapeutic applications.

A. Double Crosslinking of Glucose Oxidase Crystals 1.0 Carbohydrate Crosslinking According to an alternate embodiment of this invention, carbohydrate crosslinked glycoprotein crystals may be of minimal solubility. In order to reduce the dissolution of protein activity from the single crosslinked glycoprotein crystals described above, the singly crosslinked crystals were submitted to a second crosslinking procedure. The second crosslinking procedure involved glutaraldehyde, or glutaraldehyde pretreated with either Tris buffer (2-amino-2-hydroxymethyl-1,3-propanediol), lysine or diaminooctane.

The crosslinking parameters for the first carbohydrate crosslinking were the same as for sample 5 and 6 described above, and shown in Table 7. The oxidation and reaction with diaminooctane steps were followed by rocking overnight at 4° C. In each case, the starting reaction contained 60 mg of protein.

TABLE 8

Protein activity of carbohydrate crosslinked glycoprotein crystals

| No. | $NaIO_4$ mg/g GO | Titrimetric activity Glucose Oxidase U/μg | | After control dissol. test | Total protein soluble in 0.1M NaOH $A_{278}$ | Solub. in NaOH % |
|---|---|---|---|---|---|---|
| | | Titr. 10 min | Titr. 30 min | | | |
| 1A. | 36 | 299 | 494 | 195 | 1.8 | 3.0 |
| 2A. | 72 | 258 | 508 | 274 | 1.8 | 3.0 |
| 3A. | 143 | 195 | 453 | 253 | 1.9 | 3.1 |
| 4A. | 143 | 76 | 88 | 151 | 20.3 | 33.8 |

The data presented in Table 8 indicate that oxidation with lower concentrations of $NaIO_4$ preserved and enhanced the protein activity of glucose oxidase in the resulting crystals most effectively. The titrimetric activities were measured after 30 minutes for crystals oxidized with either 36 or 72 mg/g GO and shown in Nos. 1A and 2A of Table 8, were 494 and 508 U/μg respectively. These values were almost twice the value of 279 U/μg obtained from GO crystals before crosslinking. The approximately 2-fold increase in glycoprotein activity obtained between sample 2A and the non-crosslinked material demonstrates that very significant enhancements of glycoprotein activity may be achieved through the carbohydrate crosslinking methods of this invention. Sample 3A was treated exactly as samples 1A and 2A except with more $NaIO_4$. For sample 4A, the washing step after oxidation was eliminated and the diaminooctane was added directly to the overnight oxidation reaction mixture. Based on this result we conclude that washing of the crystals after oxidation and before crosslinking is critical.

1.1 Solubility in 0.1 M NaOH

The solubility of the crosslinked crystals in 0.1 NaOH was measured using 1 ml of crosslinked crystals. The crystals were initially centrifuged and then resuspended in 1 ml of 0.1 M NaOH. After a two hour incubation, the supernatant was clarified by centrifugation and the protein A 278 was measured from supernatant, as shown in Tables 8 and 9.

1.2 Solubility in Phosphate Buffer

We measured the solubility of the double crosslinked glycoprotein crystals using a controlled dissolution test. A 1 ml sample of crosslinked crystals was suspended in 2 mM sodium phosphate buffer (pH 7.0) and then diluted in 4 ml of 0.2 M glucose in 2 mM sodium phosphate buffer at pH 7.0. The crystal samples were then incubated overnight at room temperature. Next the crystals were collected by centrifugation at 5,000 rpm for 10 min, after which activity was measured by titration and the results are shown in Tables 8 and 9. After the first crosslinking, approximately one-half of the glucose oxidase catalytic activity was dissolved in the substrate buffer during the controlled dissolution test which lasts 30 minutes. The other half remained with the crystals.-

2.0 Amino Acid Side Chain Functional Group Crosslinking

The second crosslinking was performed using aliquots of the most active sample (no. 2A.) of the first crosslinking experiment shown in Table 8. Glycoprotein amino acid side chain functional group crosslinking reagents were added to the carbohydrate crosslinked glycoprotein crystals suspended in 0.2 M sodium phosphate at pH 7.0. Reactions were allowed to proceed for two hours at room temperature, with each second crosslinking reagent described below. We found that centrifugation was not a preferred method for recovering all the crystal material after washing. Therefore the crystals were filtered and washed over glass fiber paper.

Protein Amino Acid Second Crosslinking Conditions for Samples Shown in Table 9

1B and 2B: Diluted glutaraldehyde was added to final concentrations of 0.2 and 0.6 g/g GO, respectively.

3B and 4B: Tris pretreated glutaraldehyde (48 mg Tris-base/g glutaraldehyde) was added to concentrations of 0.2 and 0.6 g/g GO crystals, respectively. In sample 4B., the washing steps after oxidation were eliminated and the diaminooctane was added directly to the oxidation mixture.

5B and 6B: First lysine and then glutaraldehyde were added to molar ratio of 4:10. Final glutaraldehyde concentrations were 0.2 and 0.6 g/g GO.

7B and 8B: Same molar ratio of glutaraldehyde and diaminooctane were added by having 15 minute incubation time between each addition. Both were added two times. Total glutaraldehyde dosages were 0.2 and 0.6 g/g GO.

TABLE 9

Protein activity of carbohydrate and protein crosslinked glycoprotein crystals

| | Titrimetric activity U/μg Glucose oxidase (GO) | | | Total | |
|---|---|---|---|---|---|
| Sample No. | Titr. 10 min | Titr. 30 min | After Controlled Dissolut. test | protein soluble in 0.1M NaOH $A_{278}$ | Solub. in NaOH % |
| 1B. | 108 | 148 | 143 | 4.0 | 6.6 |
| 2B. | 110 | 187 | 156 | 3.9 | 6.6 |
| 3B. | 111 | 210 | 112 | 4.0 | 6.7 |
| 4B. | 127 | 259 | 181 | 4.0 | 6.6 |
| 5B. | 145 | 293 | 150 | 4.1 | 6.8 |
| 6B. | 146 | 258 | 168 | 3.9 | 6.5 |
| 7B. | 105 | 178 | 154 | 1.9 | 3.1 |
| 8B. | 107 | 98 | 155 | 1.2 | 2.1 |

In summary, glucose oxidase crystals were crosslinked with methods including single carbohydrate crosslinking, or single carbohydrate crosslinking followed by either glutaraldehyde crosslinking, tris pretreated glutaraldehyde crosslinking, a combination of lysine and glutaraldehyde crosslinking, and sequential and repeated glutaraldehyde and diaminooctane crosslinking. All of the methods produced controlled dissolution crystals with high enzymatic activity. In each case the second crosslinking reduced the activity of the crystals, but also reduced the solubility in the controlled dissolution buffer. In samples 1B through 6B, the solubility in 0.1 M NaOH was increased. In contrast, the results with sample Nos. 7A and 7B, in which the second crosslinking was performed using the combination of glutaraldehyde and diaminooctane, showed reductions in the solubility of the crystals in both the controlled dissolution test and in 0.1 M NaOH. Microscopic examination of the double crosslinked crystals revealed that all samples looked similar, with sharp shaped crystals that were yellow colored and some of them were broken. Thus, it appears the crystalline form was well preserved during the crosslinking procedures.

Those of skill in the art will appreciate that variations on the methods described here can be used to produce highly insoluble carbohydrate crosslinked glycoprotein crystals. For example, optimization of the pH conditions during the oxidation reaction step, manipulation of the oxidant concentration and time of reaction, and performance of the reduction reaction step will reduce the controlled dissolution properties of the crystals. Likewise, alternating an optimized carbohydrate crosslinking with one or more pH optimized pretreated glutaraldehyde or other multifunctional crosslinking steps will greatly increase the insolubility, while maintaining activity.

Example 3

Preparation of Gluconic Acid Using Carbohydrate Crosslinked Glucose Oxidase Crystals Carbohydrate crosslinked glucose oxidase crystals, prepared as described above, are useful in the preparation of gluconic acid. Prior to use they may be stored in phosphate buffer pH 6.2 containing 40% of ethanol to prevent microbial growth. The amount of enzyme in each example is measured as a volume of homogenous slurry. The slurry is first washed with water on a membrane filter to remove ethanol and buffer. The carbohydrate crosslinked glucose oxidase crystals are added as washed cake from the membrane directly to a stirred batch of glucose solution to start the reaction. The dry substance of the carbohydrate crosslinked glucose oxidase crystal slurry is 25 mg/ml.

The effects of aeration and stirring are studied prior to setting up the standard conditions. A single batch of 1 M glucose solution is used. The batch is first aerated at a low rate (0.6 1/min) and stirred at a low speed (100 rpm). The rate of the reaction is followed until it is stable. Then, aeration and stirring are increased successively to provide a variety of combinations of aeration and stirring conditions. The reaction rates at each aeration-stirring combination are recorded. The catalyzed reaction is highly limited by the availability of oxygen. Thus, the stirring and aeration must be very effective. The aeration and stirring which provide the maximum reaction rate are selected for use as the standard conditions.

The gluconic acid production process is performed at different concentrations of glucose. The same amount of carbohydrate crosslinked glucose oxidase crystals (500 mg dry substance) are used in each example. The process is carried out over a period of 300–600 minutes. Only the 100 g/l experiment is run to 100% conversion.

A glucose concentration of 100 g/l is selected as standard for comparison of the effects of the other parameters. The linear progress of the reaction in the 100 g/l experiment indicates that glucose concentration is not the limiting factor.

The effect of pH is studied in the range of 4 to 9. The pH of each experiment is adjusted by the set point of the titrator. No buffer is used. The reaction rate is favorable between pH 5 and 8. The rate is decreased to 50% at pH 4 and 9.

The amount of carbohydrate crosslinked glucose oxidase crystal used is varied between 125 and 1250 mg in the standard batches. As the amount of carbohydrate crosslinked glucose oxidase crystals increase from 125 to 500 mg, the reaction rate increases in direct proportion. The highest dose of carbohydrate crosslinked glucose oxidase crystals, 1250 mg, does not increase the reaction rate beyond that realized using 500 mg.

The effect of catalase is studied by adding either 0.0 ml, 0.1 ml or 0.3 ml to the reaction. An industrial catalase is used for comparison: Genencor CAT HP L5000, Lot No. 6094186026, date APR 11.95. Activity 5000 Baker units per ml. One unit will decompose 264 mg (7.76 millimoles) hydrogen peroxide in one hour at 25° C.

The highest dosage of catalase decomposes 194 millimoles of hydrogen peroxide per minute, which is more than 200 times the activity of glucose oxidase, 0.91 mmol/min, in this experiment. However, catalase addition has no significant effect on the reaction rate. The carbohydrate crosslinked glucose oxidase crystals decompose the hydrogen peroxide which is produced in the reaction.

Gluconic acid production at three different temperatures (10, 25 and 30° C.) are studied using standard conditions. The rate of reaction is approximately the same at 25 and 30° C., but significantly lower at 10° C. The solubility of oxygen may decrease at higher temperatures and may becoming a limiting factor.

Example 4

Preparation of Crosslinked Candida Rugosa Crystals

A. Crystallization of Candida Rugosa Lipase

A 5 kg aliquot of Candida rugosa lipase ("CRL") in powder form (Meito) was mixed with 5 kg celite and dissolved in 102 L distilled deionized water and the volume brought to 200 L with distilled deionized water. The suspension was mixed in an Air Drive Lightning Mixer for 2 hours at room temperature and then filtered through a 0.5 micron filter to remove celite. The mixture was then ultra-filtered and concentrated to 14 L (469 g) using a 3K hollow fiber filter membrane cartridge. Solid calcium acetate was added to a concentration of 5 mM $Ca(CH_3COO)_2$. The pH was adjusted to pH 5.5 with concentrated acetic acid, as necessary. A 7 liter aliquot was crystallized by either addition of 1.75 liters of 2-methyl-2,4-pentanediol ("MPD") or by addition of 3.5 liters of a 30% solution of PEG-8000. The resulting solution was mixed and crystallization allowed to proceed overnight at ambient temperature for about 17–20 hrs. The crystal yield was about 70%.

B. Carbohydrate Crosslinking of Candida Rugosa Lipase 244 mg of enzyme crystals were suspended in 2 ml of 50 mM sodium acetate, 5 mM $CaCl_2$, and 10% polyethylene glycol at pH 5.5. The crystals were then oxidized with 2–15 mg of sodium periodate ($NaIO_4$) for 2 hours at room temperature and overnight at 0C. Oxidation was followed by dialysis in the 50 mM sodium acetate, 5 mM $CaCl_2$, and 10% polyethylene glycol at pH 5.5 to remove periodate. The oxidized crystals were exposed to 200 μL of an 0.8 M solution of ethylenediamine solution in 50 mM Tris, 5 mM $CaCl_2$ at pH 8.0 and the reaction was allowed to proceed for 2 hours. The mixture was acidified to pH 6.0 using 1 N HCl and then 20 μl of 0.1 M $NaCNBH_3$ was added at the end of 2 hours. The reaction was allowed to proceed for another 30 minutes. The protein was then washed several times with 10 mM Tris, 10 mM $CaCl_2$ at pH 6.0 and suspended in the same buffer. The modified samples were insoluble in 10 mM Tris, 10 mM $CaCl_2$ at pH between 6 and 7, but were soluble when the pH was raised to 8.5 or higher. They retained a high level of original activity towards p-nitrophenyl acetate. The activity was followed spectrophotometrically at 410 nm for the release of p-nitrophenol. The assay solution had 1 mM of p-nitrophenylacetate in 50 mM sodium acetate buffer at pH 6.5. The extinction coefficient of p-nitrophenol at this pH is 2,500 $M^{-1}cm^{-1}$.

It should be understood that the solubility of the protein may be efficiently controlled at each stage of the above-described process by varying the reaction conditions to achieve a different extent or degree of oxidation and by changing the stoichiometry and hydrophobicity of the diamine component (e.g., changing from ethylene diamine to hexane diamine).

In one example, 875 mg of Candida rugosa. lipase in 35 ml of 0.05 M acetate, 10% PEG 8000 pH 5.5 was oxidized with 200 mg of sodium periodate for two hours at room temperature or overnight at 0° C. After oxidation, the crystals were dialyzed in 10 mM Tris, 10% PEG 8000 to remove the periodate. The oxidized crystals were then incubated with 14 mls of a 1 M solution hexanediamine hydrochloride at pH 8 and 315 μl of 1 N NaOH was added to the dialyzed enzyme and Schiff-base formation was allowed to proceed for 6 hrs at room temperature. The reaction mix was acidified to pH 6 with 1 N HCl, requiring approximately 400 μl of 1 N HCl and 400 mg of solid $NaCNBH_3$ was added. The reduction reaction was allowed to proceed for 90 minutes at room temperature. Next the mixture was centrifuged and washed 4 times with 10 mM $CaCl_2$. The crosslinked enzyme was stored in 10 mM Tris, 10 mM $CaCl_2$ at pH 7.0.

This crosslinked sample can be further modified with glutaraldehyde and/or other reagents as shown below. Further modifications by glutaraldehyde and other reagents may occur either at the amino groups introduced at the surface or possibly at amino groups within amino acid side chains.

In another example, 75 mg of the crosslinked sample from above was suspended in 0.5 ml of 10 mM $CaCl_2$ at pH 7.0. Next 50 μl of a 25% pretreated glutaraldehyde solution was added and the reaction was allowed to proceed for 18 hours at room temperature. Pretreated glutaraldahyde was prepared by mixing 1:1 of 50% glutaradahyde with 0.3 M Borate buffer at pH 8.5 and heating at 50° C. for 1 hour. The reaction was terminated by centrifugation of the slurry, followed by decanting of the supernatant, and washing of the glycoprotein crystals four times with 10 mM Tris, 10 mM $CaCl_2$ at pH 7.0.

Two different simultaneous surface modifications can be introduced onto the oxidized glycoprotein crystals using two different crosslinking reagents. This entails simultaneous addition of pretreated glutaraldehyde (12 μl of a 25% solution) and 2% (w/v) of a second reagent which was either succinic anhydride, phenylglutaric anhydride, salicylaldehyde, acetimidate, formalin, acrolein, succinic semialdehyde, butyraldehyde, dodecylaldehyde, glyceraldehyde or trans-oct-2-enal. to 75 mg of crystals in 0.5 ml of 10 mM $CaCl_2$ at pH 7.0. All reactions were carried out at pH 7.5–8.0 for twenty four hours at room temperature with shaking. The reaction was terminated by centrifugation of the crystals, decanting of the supernatant and subsequently followed by five washes with 10 mM $CaCl_2$ at pH 7.0.

All of the samples of Candida rugosa lipase crosslinked via the carbohydrate method were insoluble and did not leach protein after a 24 hr incubation period at 40° C. in 10 mM Tris, 10 mM $CaCl_2$ at pH 7.0.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A crosslinked glycoprotein crystal, said crosslinked glycoprotein crystal having each of the following characteristics:
    (a) said crosslinked glycoprotein crystal comprises a three dimensional crystal lattice;
    (b) said crosslinked glycoprotein crystal is in a shape selected from the group consisting of spheres, needles, rods, plates, rhomboids, cubes, bipyramids and prisms;
    (c) said crosslinked glycoprotein crystal is crosslinked through carbohydrate-to-carbohydrate crosslinking of one or more carbohydrate moieties within the crystal lattice; and
    (d) said crosslinked glycoprotein crystal displays enhanced stability as compared to an uncrosslinked counterpart glycoprotein.

2. The crosslinked glycoprotein crystal according to claim 1, wherein said crystal is crosslinked with a multifunctional crosslinking agent.

3. The crosslinked glycoprotein crystal according to claim 1, said glycoprotein crystal being substantially insoluble and stable in a composition under storage conditions and substantially soluble and active under conditions of use of said composition.

4. The crosslinked glycoprotein crystal according to claim 1, said glycoprotein crystal being capable of releasing its protein activity at a controlled rate upon exposure to a change in the environment surrounding said crystal, said change being selected from the group consisting of change in pH, change in solute concentration, change in temperature, change in chemical composition, change in shear force acting upon the crystals and combinations thereof.

5. The crosslinked glycoprotein crystal according to claim 1, wherein said crystal is crosslinked with a diamine crosslinking agent.

6. The crosslinked glycoprotein crystal according to claim 5, wherein said diamine crosslinking agent is selected from the group consisting of hexamethylenediamine, diaminooctane, and ethylenediamine.

7. The crosslinked glycoprotein crystal according to claim 1, wherein said glycoprotein is an enzyme which is selected from the group consisting of lipases and oxidases.

8. The crosslinked glycoprotein crystal according to claim 7, wherein said enzyme is glucose oxidase.

9. The crosslinked glycoprotein crystal according to claim 2, wherein said enzyme is *Candida rugosa* lipase.

10. The crosslinked glycoprotein crystal according to claim 1, said crystal being further crosslinked through one or more amino acid side chain functional groups in said glycoprotein.

11. The crosslinked glycoprotein crystal according to claim 10, wherein said crystal is crosslinked through one or more carbohydrate moieties in said glycoprotein with a diamine crosslinking agent and said crystal is crosslinked through one or more amino acid side chain functional groups in said glycoprotein with a multifunctional crosslinking agent.

12. The crosslinked glycoprotein crystal according to claim 11, wherein said diamine crosslinking agent is selected from the group consisting of hexamethylenediamine and diaminooctane and wherein said multifunctional crosslinking agent is selected from the group consisting of glutaraldehyde, succinic anhydride, phenylglutaric anhydride, salicylaldehyde, acetimidate, formalin, acrolein, succinic semialdehyde, butyraldehyde, dodecylaldehyde, glyceraldehyde or trans-oct-2-enal.

13. The crosslinked glycoprotein crystal according to claim 1 or 10, said glycoprotein crystal having at least about 2 fold greater stability as measured by pronase digestion, thermal stability, or activity in 50% ethanol than the soluble form of the glycoprotein that is crystallized to form said glycoprotein crystal that is crosslinked.

14. The crosslinked glycoprotein crystal according to claim 13, wherein the stability of said glycoprotein crystal is at least about 5 to about 10 times that of the soluble form of the glycoprotein that is crystallized to form said glycoprotein crystal that is crosslinked.

15. The crosslinked glycoprotein crystal according to claim 1 or 10, said glycoprotein crystal having greater stability at an alkaline pH or an acidic pH than the soluble form of the glycoprotein that is crystallized to form said glycoprotein crystal that is crosslinked.

16. The crosslinked glycoprotein crystal according to claim 1 or 10, said glycoprotein crystal having greater stability at high temperature than the soluble form of the glycoprotein that is crystallized to form said glycoprotein crystal that is crosslinked.

17. The crosslinked glycoprotein crystal according to claim 1 or 10, said glycoprotein crystal having activity in an organic solvent or aqueous-organic solvent mixture that is at least about 2 times greater than the activity of an equivalent amount of the soluble form of the glycoprotein that is crystallized to form said glycoprotein crystal that is crosslinked.

18. The crosslinked glycoprotein crystal according to claim 1 or 10, said crystal having a longest dimension of between about 0.01 $\mu$m and about 500 $\mu$m.

19. The crosslinked glycoprotein crystal according to claim 15, said crystal having a longest dimension of between about 0.1 $\mu$m and about 50 $\mu$m.

20. A method for producing a crosslinked glycoprotein crystal comprising the steps of:
    (a) reacting a glycoprotein crystal with an oxidizing agent to oxidize the carbohydrate moieties of said glycoprotein; and
    (b) reacting said glycoprotein crystal with a crosslinking agent, under conditions sufficient to induce crosslinking of said crystal through said carbohydrate moieties of said glycoprotein.

21. The method for producing a crosslinked glycoprotein crystal according to claim 20, wherein said crosslinking agent is a multifunctional crosslinking agent.

22. The method for producing a crosslinked glycoprotein crystal according to claim 20, wherein said oxidizing agent is sodium periodate ($NaIO_4$).

23. The method for producing a crosslinked glycoprotein crystal according to claim 20, wherein said crosslinking agent is a diamine crosslinking agent.

24. The method for producing a crosslinked glycoprotein crystal according to claim 23, wherein said diamine crosslinking agent is selected from the group consisting of hexamethylenediamine, diaminooctane, and ethylenediamine.

* * * * *

UNITED STATES PATENT AND TRADEMARK OFFICE
CERTIFICATE OF CORRECTION

PATENT NO. : 6,359,118 B2
DATED : March 19, 2002
INVENTOR(S) : Alexey L. Margolin et al.

It is certified that error appears in the above-identified patent and that said Letters Patent is hereby corrected as shown below:

Title page,
Item [56], References Cited, OTHER PUBLICATIONS, change "Vilenchi" to -- Vilenchik --; change "McPherron" to -- McPherson --; and change "*Methods of Biochemical Analyson*" to -- *Methods of Biochemical Analysis* --.

Column 2,
Line 48, change "Ouart" to -- Quart --;

Column 4,
Line 50, change "alycoprotein" to -- glycoprotein --;

Column 5,
Line 19, change "alycoprotein" to -- glycoprotein --;

Column 10,
Line 9, change "know" to -- known --;

Column 15,
Line 64, change "al least" to -- at least --;

Column 18,
Line 62, change "150" to -- 15% --;

Column 20,
Line 34, change "TABLE 8" to -- TABLE 5 --;
Line 58, change "that are obtained" to -- that obtained --;

Column 24,
Line 12, change "that he" to -- that the --;

Column 29,
Line 19, change "becoming" to -- become --;
Line 48, change "at OC" to -- at O°C --;

UNITED STATES PATENT AND TRADEMARK OFFICE
CERTIFICATE OF CORRECTION

PATENT NO. : 6,359,118 B2
DATED : March 19, 2002
INVENTOR(S) : Alexey L. Margolin et al.

It is certified that error appears in the above-identified patent and that said Letters Patent is hereby corrected as shown below:

Column 31,
Line 47, change "2" to -- 7 --; and

Column 32,
Line 37, change "15" to -- 18 --.

Signed and Sealed this

Twenty-third Day of March, 2004

JON W. DUDAS
*Acting Director of the United States Patent and Trademark Office*